(12) United States Patent
Vuksan

(10) Patent No.: US 7,326,404 B2
(45) Date of Patent: Feb. 5, 2008

(54) KONJAC-MANNAN AND GINSENG COMPOSITIONS AND METHODS AND USES THEREOF

(75) Inventor: Vladimir Vuksan, Toronto (CA)

(73) Assignee: Vuksan Holdings Inc., Toronto, Ontario (CA)

( * ) Notice: Subject to any disclaimer, the term of this patent is extended or adjusted under 35 U.S.C. 154(b) by 0 days.

(21) Appl. No.: 10/296,196

(22) PCT Filed: May 31, 2001

(86) PCT No.: PCT/CA01/00774

§ 371 (c)(1),
(2), (4) Date: Jul. 7, 2003

(87) PCT Pub. No.: WO01/91586

PCT Pub. Date: Dec. 6, 2001

(65) Prior Publication Data

US 2005/0020535 A1      Jan. 27, 2005

Related U.S. Application Data

(60) Provisional application No. 60/208,090, filed on May 31, 2000.

(51) Int. Cl.
*A61B 5/055* (2006.01)
*A61K 47/00* (2006.01)
*A61K 9/14* (2006.01)
(52) U.S. Cl. .................... 424/9.35; 424/439; 424/489
(58) Field of Classification Search ............... 424/195, 424/180, 725–779
See application file for complete search history.

(56) References Cited

U.S. PATENT DOCUMENTS 3,856,945 A * 12/1974 Sugiyama et al. .......... 424/773
4,882,160 A * 11/1989 Yang et al. ................. 424/440
5,633,030 A    5/1997 Marrs et al.
6,048,532 A    4/2000 Naranjo et al.
6,210,686 B1 *  4/2001 Bell et al. .................. 424/400
6,733,769 B1 *  5/2004 Ryan et al. ................. 424/439
6,774,111 B1 *  8/2004 Wolf et al. .................. 514/23

FOREIGN PATENT DOCUMENTS

JP           10028554 A  *  2/1998

OTHER PUBLICATIONS

Eliasson K, Ryttig KR, Hylander B, Rossner S: "A dietary fibre supplement in the treatment of mild hypertension. A randomized, double-blind, placebo controlled trial." J Hypertens 10:195-199, 1992.
American Diabetes Association (ADA): Nutrition Recommendations and principles for people with diabetes mellitus. Diabetes care 22:S42-S43, 1999.
Anderson JW, Tietyen-Clark J: Dietary fiber: hyperlipidemia, hypertension, and coronary heart disease, Am J Gastroenterol 81:907-919, 1988.
Aro A, UUsitupa M, Voutilainen E, Hersio K, Korhonen T, Siitonen O: Improved diabetic control and hypocholesterolaemic effect induced by long-term dietary supplementation with guar gum in type 2 (insulin-independent) diabetes. Diabetologia 21:29-33, 1981.
Arvill A, Bodin L: Effect of short-term ingestion of Konjac glucomannan on serum cholesterol in healthy men. Am J Clin Nutr 61:585-589, 1995.
Brown L, Rosner B, Willett WW, Sacks FM: Cholesterol-lowering effects of dietary fiber: a meta-analysis, Am J Clin Nutr 69:30-42, 1999.
Burt VL, Cutler JA, Higgins M, Horan MJ, LaBarthe D, Whelton P, Brown C, Rocella EJ: Trends in the prevalence, awareness, treatment and control of hypertension in the adult US population: data from the Health Examination Surveys, 1960-1991. Hypertension 26:60-69, 1995.
DCCT Research Group: The effect of intensive treatment of diabetes on the development and progression of long-term complications in insulin-dependent diabetes mellitus. The diabetes control and complications trial. New Engl J Med 329:977-986, 1993.
Doi K, Matsuura M, Kawara A, Baba S: Treatment of diabetes with glucomannan Konjac mannan. Lancet 1:987-988, 1979.
Eastwood MA, Morris ER. Physical properties of dietary fiber that influence physiological function: a model for polymers along gastrointestinal tract. Am J Clin Nutr 55:436-442, 1992.
Ebihara K, Masuhara R Kiriyama S: Major determinants Plasma glucose-flattening activity of a water-soluble dietary fiber: effects of konjac mannan on gastric emptying and intraluminal glucose diffusion. Nutr Reports Intl 23:1145-1156, 1981.
Ebihara K, Schneeman BO: Interaction of bile acids, phospholipids, cholesterol and triglycerides with dietary fibers in the small intestine of rats. J Nutr 119:1100-1106, 1989.
Executive Summary of the Third Report of the National Cholesterol Education Program (NCEP) Expert Panel on Detection, Evaluation, and Treatment of High Blood Cholesterol in Adults. JAMA; 285:2486-2497, 2001.

(Continued)

Primary Examiner—S. Tran
(74) Attorney, Agent, or Firm—Bereskin & Parr

(57) ABSTRACT

The present invention relates to a number of compositions namely a *konjac*-mannan mixture, a ginseng composition and a composition comprising *konjac*-mannan and American ginseng. Methods of use are described including their use for reducing blood glucose in non-diabetic and diabetic individuals, as well as reducing postprandial blood glucose in such individuals. Applications in the treatment of hyperlipidemia, high blood pressure, an increase in nitric oxide, syndrome X and cardiovascular disease are also described. Various other applications of the composition and methods are also described.

13 Claims, 19 Drawing Sheets

OTHER PUBLICATIONS

Friedewald WT, Levy RI, Fridrickson DS: Estimation of plasma low-density lipoproteins, cholesterol concentration without use of the preparative ultracentrifuge. Clin Chem 18:499-502, 1972.

Fruchart JC, Kora I, Cachera C, Clavey V, Duthilleul P, Moschetto Y: Simultaneous measurements of plasma apolipoproteins A-1 and B by electroimmunoassay. Clin Chem 28:59-62, 1982.

Goldsmith MG, Barrett-Connor E, Edelstein SL, Wingard DL, Cobin BT, Herrman WH: Dislipidemia and ischemic heart disease mortality among men and women with diabetes. Circulation 89:991-997, 1994.

Gu K, Cowie CC, Harris MI: Mortality in Adults With and Without Diabetes in a National Cohort of the U.S. Population, 1971-1993. Diabetes Care 21:1138-1145, 1998.

Haffner SM, Stern MP, Hazuda HP, Rosenthal M, Knapp JA, Malina RM: Role of obesity and fat distribution in non-insulin-dependent diabetes mellitus in Mexican Americans and non-Hispanic whites. Diabetes Care 9:153-161, 1986.

Haffner SM, Stern MP, Hazuda HP, Mitchell BD, Patterson JK: Cardiovascular risk factors in confirmed prediabetic individuals. Does the clock for coronary heart disease start ticking before the onset of clinical diabetes? JAMA 263:2893-8, 1990.

Haffner SM, Lehto S, Ronnemaa T, Pyorala K, Laakso M: Mortality from coronary heart disease in subjects with type 2 diabetes and in nondiabetic subjects with and without prior myocardial infarction. N Engl Med 339:229-34, 1998.

Harris MI, Flegal CM, Cowle CC, Eberhardt MS, Goldstein DE, Little RR, Weidmeyer H-M, Byrd-Holt DD: Prevalence of diabetes, impaired fasting glucose, and impaired glucose tolerance in U.S. adults: The Third National Health and Nutrition Survey, 1988-1994. Diabetes Care 21(4):518-524, 1998.

Helmrich SP, Ragland DR, Leung RW, Paffenbarger RS Jr: Physical activity and reduced occurrence of non-insulin-dependent diabetes mellitus. N Engl J Med 325:147-152, 1991.

Himsworth H: Diabetes mellitus: a differentiation into insulin-sensitive and insulin-insensitive types. Lancet i:127-130, 1936.

Hunninghake DB, Stein EA, Dujovne CA, Harris WS, Feldman EB, Miller VT, Tobert JA, Laskarzewski PM, Quiter E, Held J, Taylor AM, Hoffer S, Leonard SB, Brewer BK: The efficacy of intensive dietary therapy alone or combined with lovastatin in outpatient with hypercholesteolemia. N Engl J Med 328:1213-1219, 1993.

Jenkins DJ, Wolever TM, Leeds AR, Gassull MA, Haisman P, Dilawari J, Goff DV, Metz GL, Alberti KG: Dietary Fibres, fibre analogues, and glucose tolerance: importance of viscosity. Br Med J 1:1392-4, 1978.

Jenkins DJA, Wolever TMS, Rao AV, Hegele RA, Mitchell SJ, Ransom TPP, Boctor DL, Spadafora PJ, Jenkins AL,Mehling C, Relle LK, Connelly PW, Story JA, Furumoto, EJ, Corey P, Wursch P: Effect on blood lipids of very high intakes of fibre in diets low in saturated fat and cholesterol. N Engl J Med. 329:21-26, 1993.

Jenkins DJA, Vuksan V, Wolever TMS, Ransom TPP, Vidgen E, Hegele RA, Leiter L, Josse RG, Abdolell, Patten R. Rao AV, Kendall CWC, Story, JA, Boctor DL, Corey PN: Diet and cardiovascular disease risk reduction: a place for fibre? Nutr Metab Cardiovasc Dis: 5:251-259, 1995.

Johnson CL, Rifkind BM, Sempos CT, Carroll MD, Bachorick PS, Briefel RR, Gordon DJ, Burt VL, Brown CD, Lippel K, Cleeman JI: Declining serum total cholesterol levels among US adults: the National Examination Surveys. JAMA 269:3002-3008, 1993.

Kiriyama S. Enishi A, Yoshida A, Suhiyama N, Shimahara H: Hypercholesterolemic activity and molecular weight of Konjac-Mannan. Nutr Reports Intl 6:231-236, 1972.

Kiriyama S, Enishi A, Yura K: Inhibitory effect of KJM on bile transport in the everted sacs from rat ileum. J Nutr 104:69-78, 1974.

Kuzuya T, Saito T, Yoshida S: Human C-peptide immunoreactivity (CPR) in blood and urine-Evaluation of radioimmunoassay method and its clinical applications. Diabetologia 12:511-518, 1976.

Landin K, Holm G, Tenghom L, Smith U: Guar gum improves insulin sensitivity, blood lipids, blood pressure, and fibrinolysis in healthy men. Am J Clin Nutr 56:1061-1065, 1992.

Livesey JH, Hodgkinson SC, Roud HR, Donald RA: Effect of time, temperature and freezing on the stability of immunoreactive LH, FSH, TSH, growth hormone, prolactin and insulin in plasma. Clin Biochem 13:151-157, 1980.

LLoyd D, Marples J: Simple Calorimetry of glycated serum protein in a centrifugal analyzer. Clin Chem 30:1686-1688, 1984.

Matsuda and DeFronzo, Diabetes Care 1999; 22:1482-70.

Modan M, Halkin H, Almog S, Lusky A, Eshkol A, Shefi M, Shitrit A, Fuchs Z: Hyperinsulinemia. A link between hypertension, obesity and glucose intolerance. J Clin Invest 75:809-817, 1985.

Morgan LM, Tredger JA, Wright J, Marks V: The effect of soluble- and insoluble-fibre supplementation on post-prandial glucose tolerance, insulin and gastric inhibitory polypeptide secretion in healthy subjects. Br J Nutr 64:103-110, 1990.

National Cholesterol Education Program: Second report of the expert panel on detection, evaluation, and treatment of high blood cholesterol in adults (adult treatment panel II). Circulation 89:1333-1445, 1994.

Olson BH, Anderson SM, Becker MP, Anderson JW, Hunninghake DB, Jenkins DJ, LaRosa JC, Rippe JM, Roberts DC, Story DB, Summerbell CD, Truswell AS, Wolever TMS, Morris DH, Fulgoni VL 3rd: Psyllium-enriched cereals lower blood total cholesterol and LDL cholesterol, but not HDL cholesterol, in hypercholesterolemic adults: results of a meta-analysis. J Nutr 127:1973-1980, 1997.

Reaven GM (1994) Syndrome X: 6 years later: J Intern Med 736:13-22, 1994.

Rimm EB, Ascherio A, Giovannucci E, Spiegelman D, Stampfer MJ, Willett WC: Vegetable, fruit, and cereal fiber intake and coronary heart disease among men. JAMA 275:447-451, 1996.

Salmeron J, Ascherio A, Rimm EB, Colditz GA, Spiegelman D, Jenkins DJ, Stampfer MJ, Wing AL, Willett WC: Dietary fiber, glycemic load and risk of NIDDM in men. Diabetes Care 20:545-550, 1997.

Salmeron J, Manson JE, Stampfer MJ, Colditz GA, Wing AL, Willett WC: Dietary fiber, glycemic load and risk of non-insulin-dependent diabetes mellitus in women. JAMA 277:472-477, 1997.

Schaefer EJ, Lichenstein AH, Lamon-Fava S, Contois JH, Li Z, Rasmussen H, McNamara JR, Ordovas JM: Efficacy of a National Cholesterol Education Program Step 2 Diet in normolipidemic and hypercholesterolemic middle-aged men and elderly men and women. Anterioscler Thromb Vasc Biol 15:1079-1083, 1995.

Shima K, Tabata M, Tanaka A, Kumahara Y: Effect of dietary fiber (guar gum and konjac powder) on diabetic control. Nutr Report Intl 26:297-302, 1982.

Shima K, Tanaka A, Ikegami H, Tabata M, Sawazaki N, Kumahara Y: Effect of dietary fiber, glucomannan, on absorption of sulfonylurea in man. Horm Metab Res 15:1-3, 1983.

Savage PJ: Cardiovascular complications of diabetes mellitus: what we know and what we need to know about prevention, Ann intern Med 124:123-126.

Stamler J, Vaccaro O, Neaton JD, Wentworth D. Diabetes, other risk factors, and 12 yr cardiovascular mortality for men in the multiple risk factor intervention trial: Diabetes Care 16:434-444, 1993.

Stefanick ML, Mackey S, Sheehan M, Ellsworth N, Haskell WL, Wood PD: Effects of diet and exercise in men and postmenopausal women with low levels of HDL cholesterol and high levels of LDL cholesterol. N Engl J Med 339:12-20, 1998.

Swain JF, Rouse IL, Curley CB, Sacks FM: Comparison of the effects of oat bran and low-fibre wheat on serum lipoprotein levels and blood pressure. N Engl J Med 322:147-152, 1990.

Terasawa F. Tsuji K, Tsuji E, Oshima S, Suzuki S, Seki M: The effects of konjac flour on the blood lipids in the eldery subjects. Japan J Nutr 37:23-28, 1979.

Trevisan M, Liu J, Bahsas FB, Menotti A: Syndrome X and mortality: A Population-based Study. Am J Epidemiol 148:958-966, 1998.

Tuomilehto J. Silvasti M, Manninen V, UUsitupa M, Aro A: Guar gum and gemfibrozil—an effective combination in the treatment of hypercholesterolemia. Atherosclerosis 78:71-77, 1989.

UK Prospective Diabetes Study (UKPDS) Group: Effect of intensive blood-glucose control with metformin on complications in overweight patients with type 2 diabetes: UKPDS 34. Lancet 352:854-865, 1998.

Uuistupa M, Tuomilehto J, karttunen P, Wolf E: Long term effects of guar gum on metabolic control, serum cholesterol and blood pressure levels in type 2 (non-insulin-dependent) diabetic patients with high blood pressure. Annals Clin Res 16:126s-131s, 1984.

Venter CS, Kruger HS, Vorster HH, Serfontein WJ, Ubbinik JB, DeVilliers LS: The effects of dietary fibre component konjac-glucomannan on serum cholesterol levels of hypercholesterolemic subjects. Human Nutr: Food Sci and Nutr 41F:55-61, 1987.

Venter CS, Vorster HH, Cummings JH: Effects of dietary propionate on carbohydrate and lipid metabolism in healthy volunteers. Am J Gastroenterol 85:549-553, 1990.

Vuksan V, Jenkins DJA, Spadafora P, Slevenpiper JL, Owen R, Vidgen E, Brighenti F, Josse RG, Leiter LA, Bruce-Thompson C: Konjac-mannan (glucomannan) improved glycemia and other associated risk factors for coronary heart disease in type 2 diabetes: A randomized controlled metabolic trial. Diabetes Care 22:913-19, 1999.

Vuksan V, Sievenpiper JL, Koo VYY, et al. American ginseng reduces postprandial glycemia in nondiabetic and diabetic individuals. Arch Intern Med 2000;160:1009-13.

Vuksan V, Stavro MP, Sievenpiper JL, Beljan-Zdravkovic U, Leiter LA, Josse RG, Zheng Xu. Similar postprandial glycemic reductions with escalations of dose and administration time of American ginseng in type 2 diabetes. Diabetes Care 2000;23:1221-6.

Vuksan V, Stavro MP, Sievenpiper JL, et al. American ginseng improves glycemia in individuals with normal glucose tolerance: Effect of dose and time escalation. J Am Coll Nutr. 2000;19:738-744.

Vuksan V, Sievenpiper JL, Xu Z, et al. American ginseng (*Panax quinquefolius* L.) attenuates postprandial glycemia in a time, but not dose, dependent manner in healthyt individuals. Am J Clin Nutr, in press.

Vuksan V, Xu Z, Jenkins AL, Beljan-Zdravkovic U, Sievenpiper JL, Letter LA, Josse RG, Stavro MP. American ginseng improves long-term glycemic control in Type 2 diabetes: Double-Blind Placebo Controlled Crossover Trial. American Diabetes Association Annual Meeting. Diabetes 2000; 49 (Suppl 1):A95.

Vuksan V, Sievenpiper JL. The variable effects of whole-leaf digitalis is a paradigm of the glycemic effects of ginseng-Reply. Arch Intern Med, 2000;160:3330-1.

Warnick GR, Bendersen J, Albers JJ: Dextran sulfate-MG (+2) precipitation procedure for quantitation of high-density lipoprotein cholesterol. Clin Chem 28: 1379-1388, 1982.

Wei M, Gaskill SP, Heffner SM, Ster MP: Effects of diabetes and level of glycemia on al-cause and cardiovascular mortality: The San Antonio Heart Study. Diabetes Care 21(7):1167-1172, 1998.

Liese AD, Mayer-Davis EJ, Haffner SM: Development of the Insulin resistance syndrome: An Epidemiologic Perspective. Epidemiol Rev 20:157-172, 1998.

McNamara JR, Schaefer EJ: Automated enzymatic standardization lipid analyses for plasma and lipid fractions. Clin Chim Acta 166:108-111, 1987.

Wolever TM, Jenkins DJA, Vuksan V, Jenkins AL, Wong GS, Josse RG: Beneficial effect of low-glycemic index diet in overweight NIDDM subjects. Diabetes Care 15(4):562-564, 1992.

Wood PJ: Physicochemical properties and physiological effects of the (1-3) (1-4)—beta-D-glucan from oats. Adv Exp Med Biol 270:119-27, 1990.

\* cited by examiner

Study Biscuits

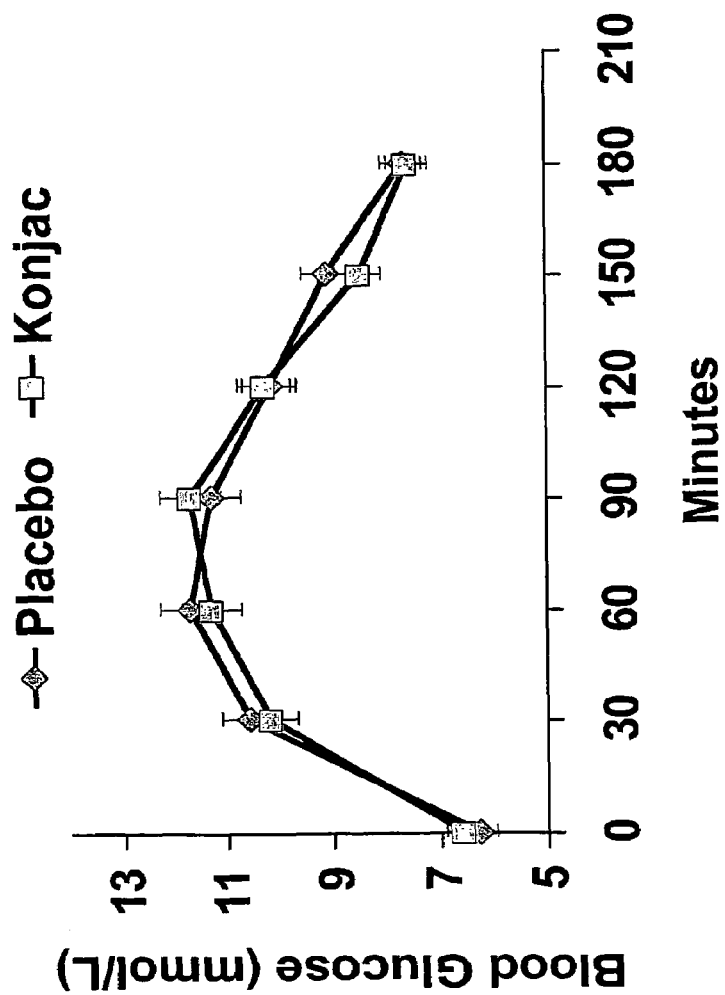

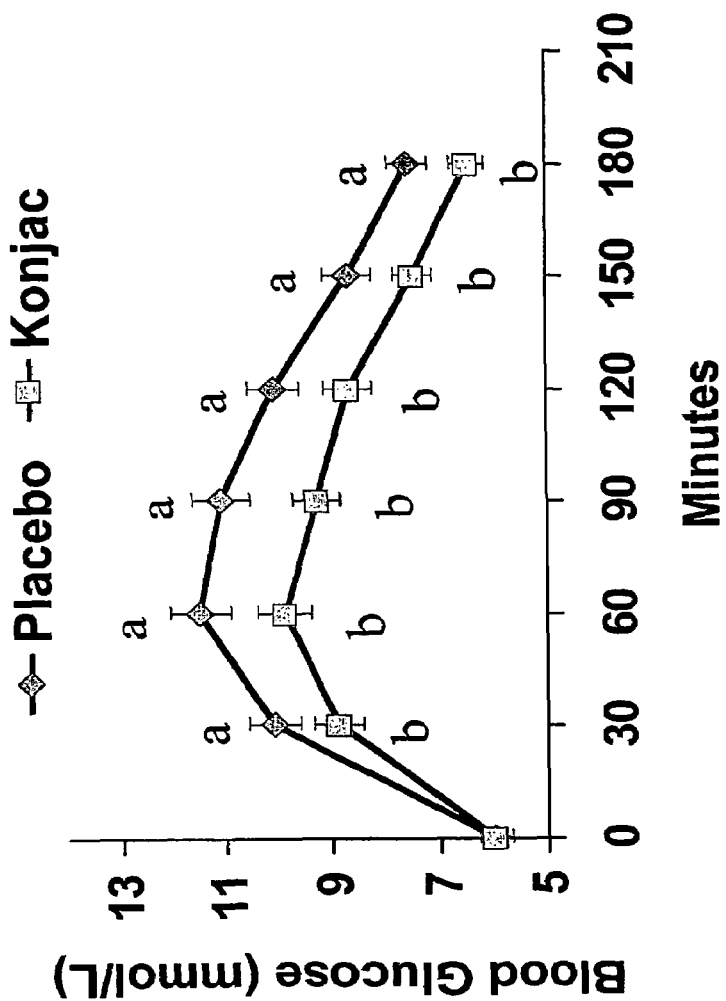

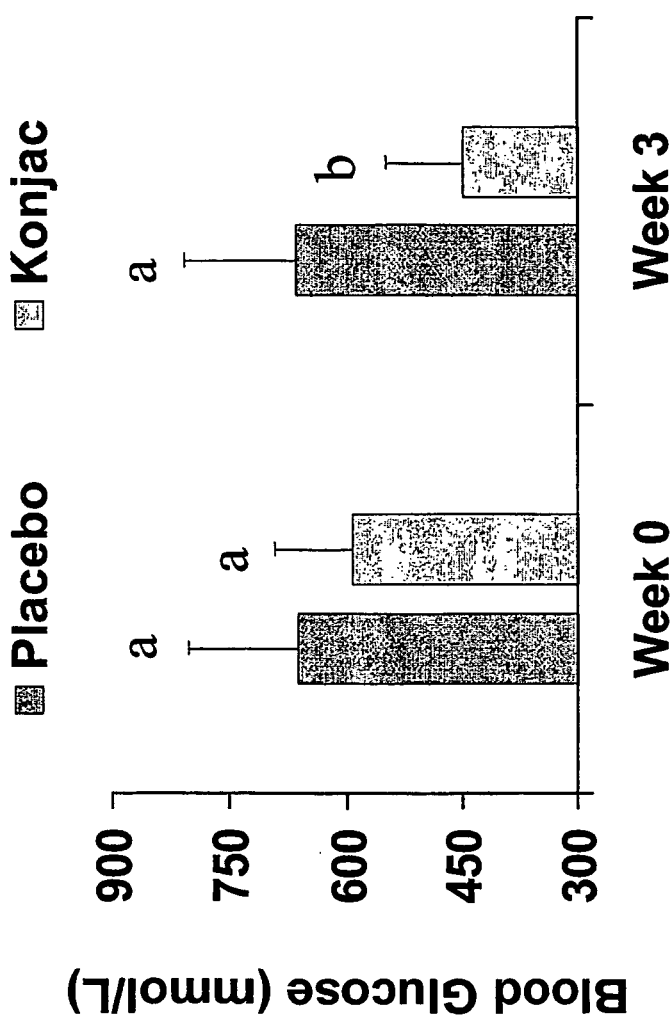

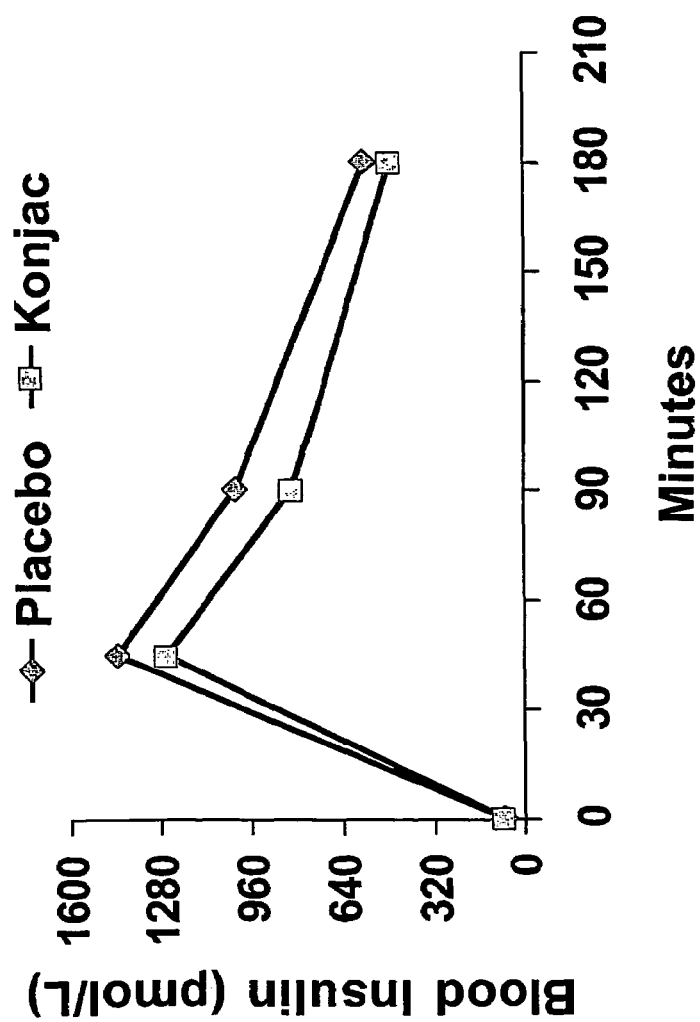

Insulin Response to a Test Breakfast After 3-Week Treatment
(Mean±SD; n=12)

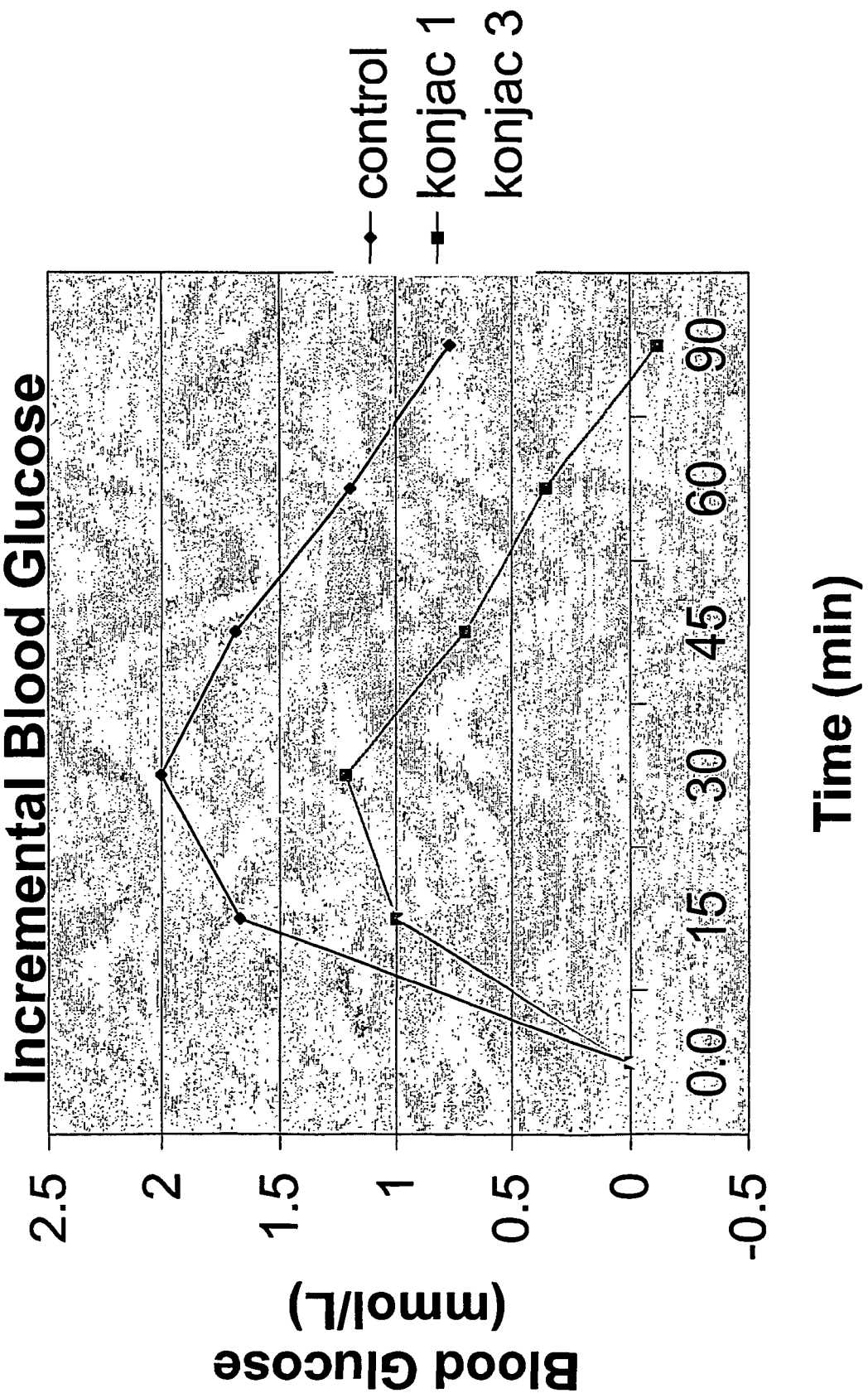

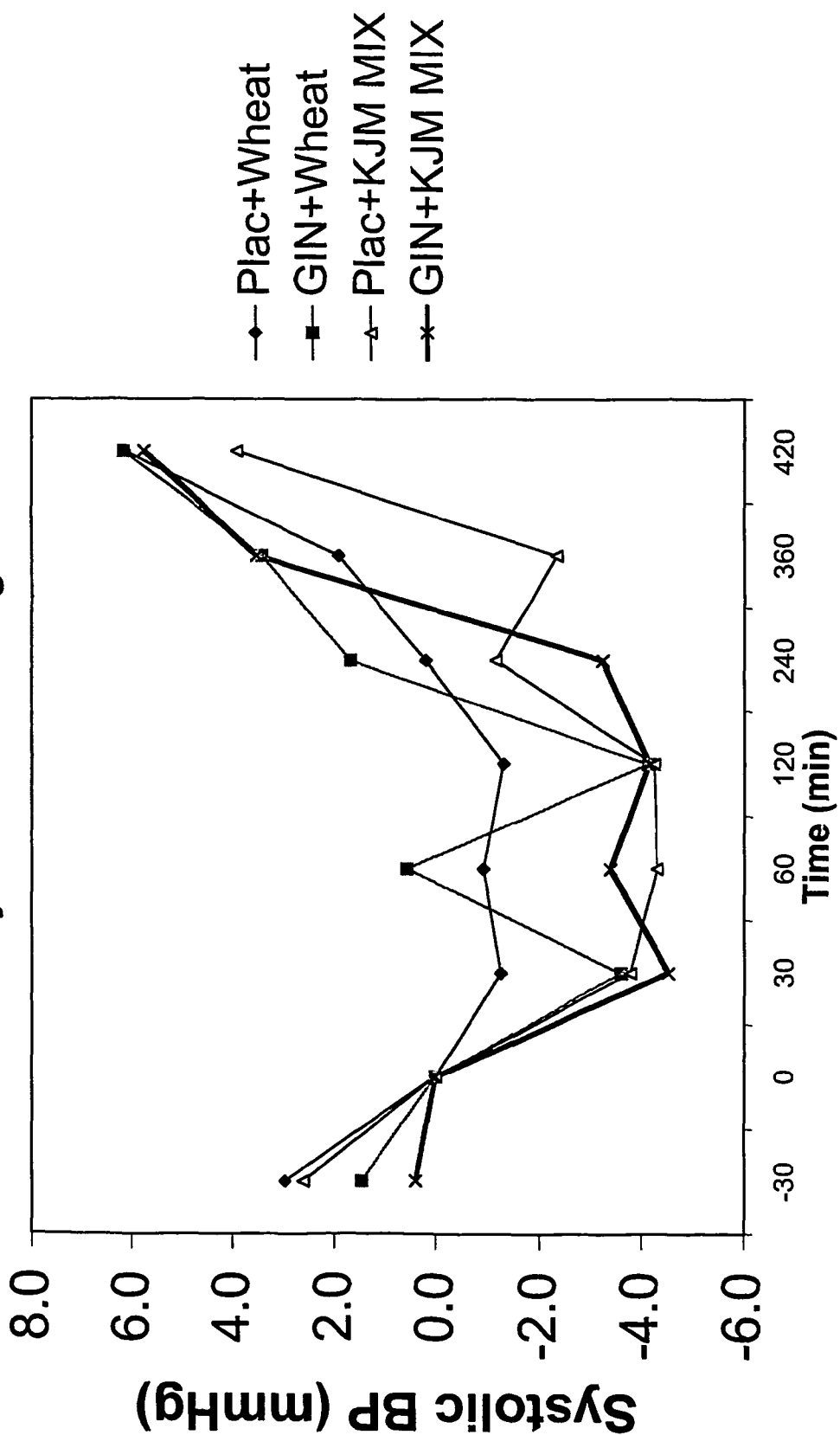

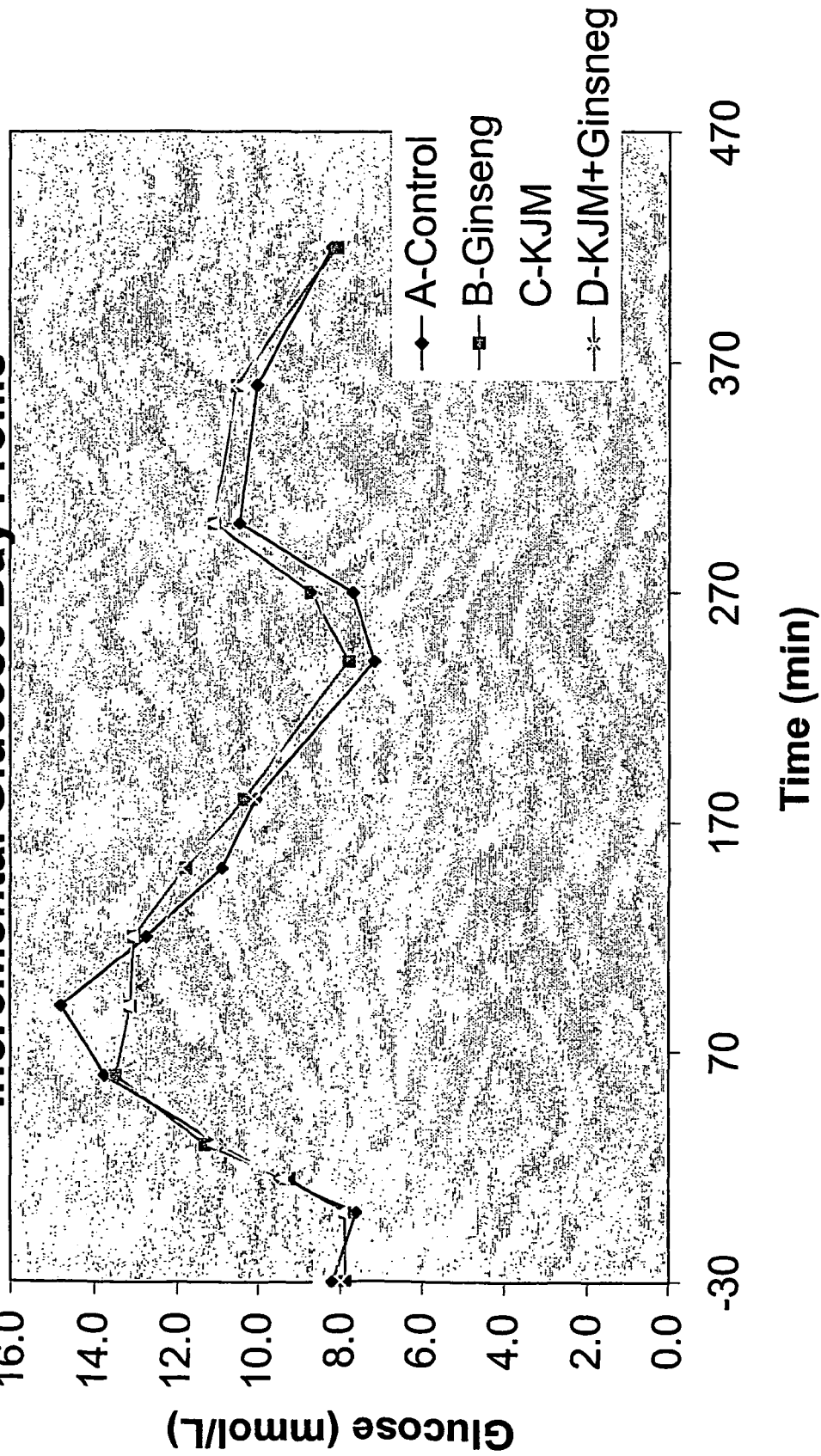

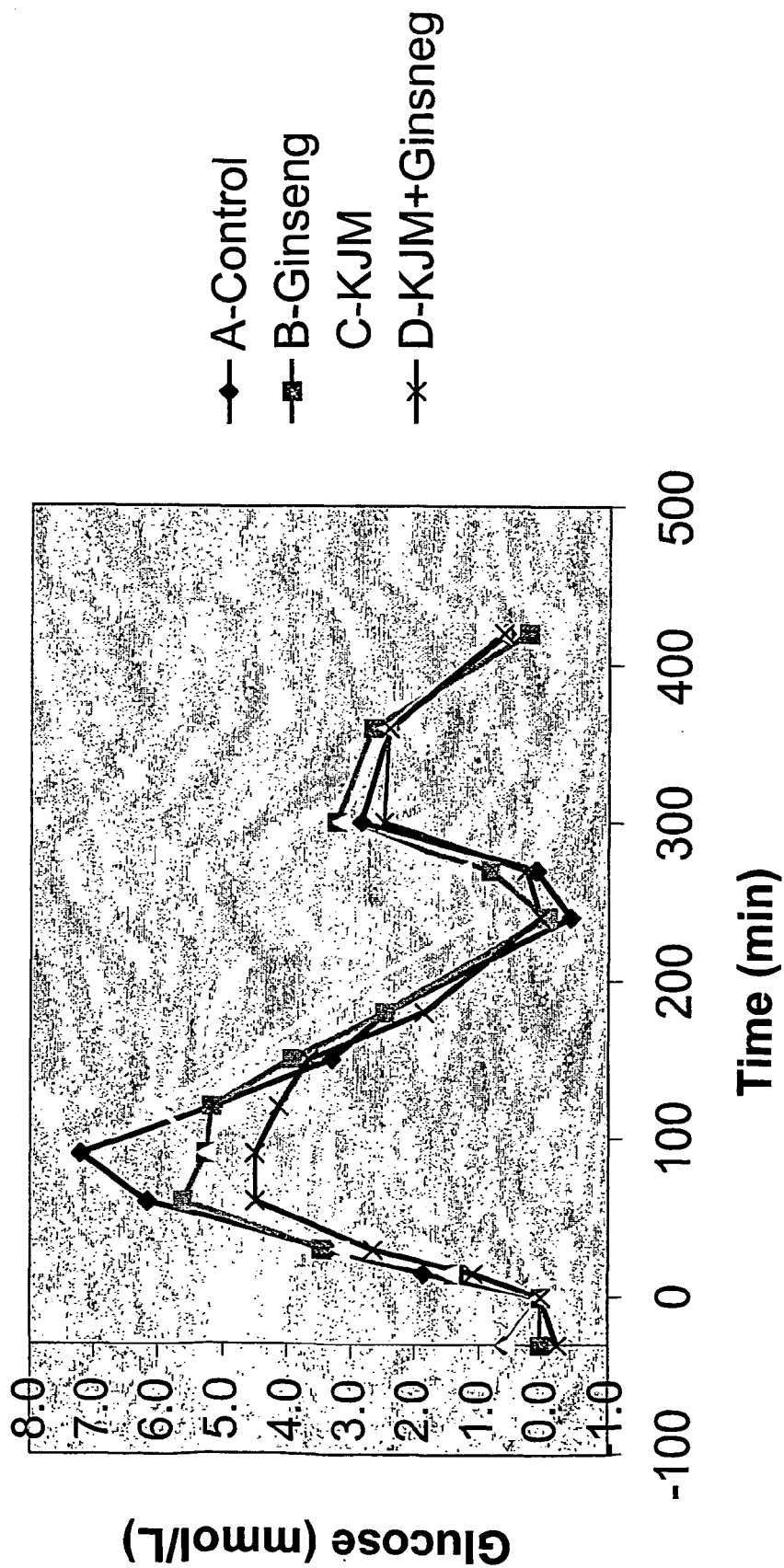

Insulin Day Profile

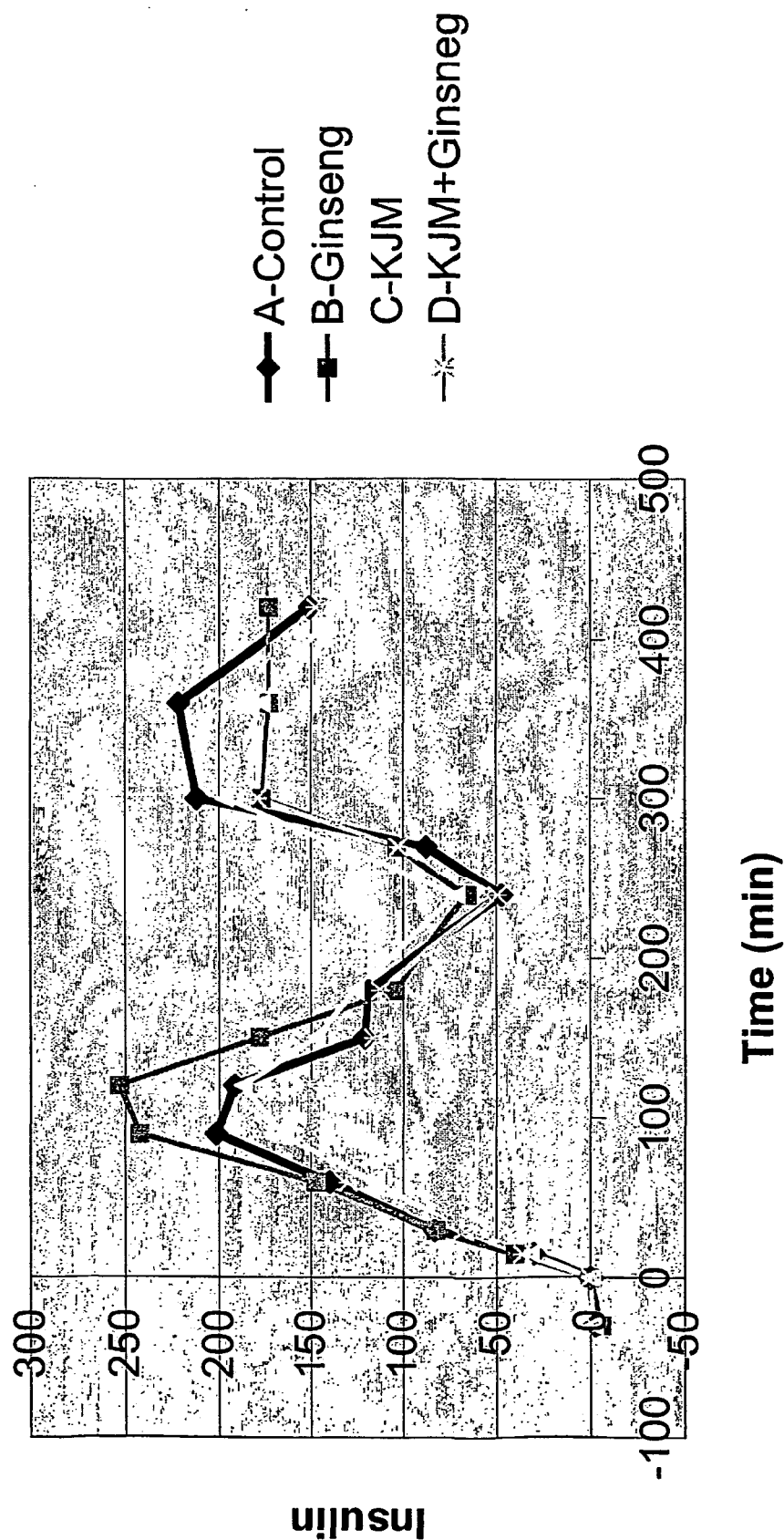

Postprandial Blood Glucose Response

KONJAC-MANNAN AND GINSENG COMPOSITIONS AND METHODS AND USES THEREOF

FIELD OF THE INVENTION

The invention relates to compositions comprising *Konjac-Mannan*, Ginseng or both and methods of use and uses of these compositions, such as in lowering blood glucose including post-prandial and long term effects. In one aspect this invention is in the field of glucose and other heart disease risk factors management. In one aspect the invention is concerned with dietary approaches to such management. In another aspect it is concerned with compositions and methods of reducing blood glucose, specifically

BACKGROUND OF THE INVENTION

Abnormal glucose tolerance and insulin resistance are related to multiple cardiovascular risk factors especially reduced HDL, elevated serum triglycerides and hypertension (Liese et al. (1998)). When clustered these is abnormalities increase the risk of coronary heart disease (CHD) morbidity and mortality, an effect that is independent of other conventional risk factors (Trevisan et al. (1998)). Co-ocurrence is usually present in insulin-insensitive individuals (Himswarth (1936)) and is often described in relation to visceral adiposity (Haffner et al. (1986)) and lack of physical activity (Helmrich 1991)). The estimated prevalence ranges from 3% (Trevisan et al. (1998)) to approximately 30% (Liese et al. (1998); Reaven (1994)) depending on how this insulin resistance-dislipidemic syndrome is defined and in which population it is measured.

Hyperglycemia and diabetes are strong and independent risk factors of both all-cause and cardiovascular (CVD) mortality (Wing et al. (1998)). These links are more pronounced when the diabetes is associated with other unfavorable risk factors such as hyperlipidemia (Goldsmith et al. (1994)), hypertension (Burt et al. (1995)), or a cluster of metabolic disorders (Stamler et al. (1993)). Since people with diabetes have almost twice the risk of dying from CVD (69.6%) compared to people in the general U.S. population (Gu et al. (1998)), the control of high glucose levels and other concomitant coronary heart disease (CHD) risk factors represents the most effective approach to prevention (Savage (1996)). The importance of stronger nutrition-hygienic measures has been stressed repeatedly for the public at large (Stamler et al. (1993); National Cholesterol Education Program: Second report of the expert panel on detection, evaluation, and treatment of high blood cholesterol in adults (adult treatment panel II). *Circulation*. 1994; 89:1333-1445)). When these measures prove inadequate, an aggressive drug therapy is often required to meet the conventional treatment guidelines (National Cholesterol Education Program: Second report of the expert panel on detection, evaluation, and treatment of high blood cholesterol in adults (adult treatment panel II). *Circulation*. 1994; 89:1333-1445)). In the general population, this approach has been shown to be effective in lowering both the prevalence of hypertension (Burt et al. (1995)) and serum cholesterol levels (Johnson et al. (1993)), but has not reduced the incidence of diabetes (Harris et al. (1998)).

Although it has been extensively described (Liese et al. (1998); Trevisan et al. 1998; Himswarth (1936); Haffner et al. (1986); Helmrich et al. (1994)), followed-up (Reaven (1994)), and had its prevalence determined (1,2), no specific recommendations for treatment of this syndrome have been proposed by health agencies. In practice, initial therapy of individual risk factors such as moderate dyslipidemia, hypertension or hyperglycemia is nonpharmacological. Treatment will often include behavioral changes to reduce body weight, increase physical activity, and moderate alcohol consumption. To achieve nutritional goals, there are three main approaches: a high-carbohydrate/low-fat diet (National Cholesterol Education Program: Second report of the expert panel on detection, evaluation, and treatment of high blood cholesterol in adults (adult treatment panel II) *Circulation* 89:1333-1445 (1994)), sharing calories between monounsaturated fat and complex carbohydrate at the expense of saturated fat (American Diabetes Association (ADA): Nutrition Recommendations and principles for people with diabetes mellitus. *Diabetes Care* 22:s42-s43 (1999)), or supplementing a high-carbohydrate/low-fat diet with exercise (Stefanick et al. (1998)).

Tighter fasting and postprandial glycemic control results in a considerable reduction in CHD and all-cause mortality (Wei et al. (1998)), as well as fewer long-term microvascular complications both in type 1 (DCCT Research Group: The effect of intensive treatment of diabetes on the development and progression of long-term complications in insulin-dependent diabetes mellitus. The diabetes control and complications trial. *New Engl J Med* 329:997-986 (1993)) and type 2 diabetes (UK Prospective Diabetes Study (UKPDS) Group: Effect of intensive blood-glucose control with metformin on complications in overweight patients with type 2 diabetes: UKPDS 34. *Lancet* 352:854-865, 1998). Effective dietary strategies shown to decrease plasma glucose excursions include the use of high fibre and low glycemic index diets (Wolever et al. (1992); Jenkins et al. (1994)). The mechanism is presumed to involve slowing carbohydrate absorption (Jenkins et al. (1994)). Based on recent population studies these types of diets have been shown to have a protective role in preventing diabetes (Salmeron et al., *Diabetes Care* 20:545-550 (1997); Salmeron et al., *JAMA* 277:472-477 (1997)) and CHD (18). In the case of clinical studies however, it is the viscous water-soluble fibers, which increase the viscosity of digesta in the human gut (Eastwood et al. (1992)) that reduce glucose and lipid CHD risk factors (Anderson et al. (1986)). Whether soluble fibre is able to reduce a cluster of risk factors is speculative. Studies using soluble fibre as an adjunct to conventional treatment in individuals with two or more major CHD risk factors are scarce (Uuistupa et al. (1984)).

Evidence suggests that fibre may also be used in a therapeutic role. Recent epidemiological findings confirm the relationship between high dietary fiber intake and lower risk of developing both diabetes (Salmeron et al. (1997); Salmeron et al. (1997)) and CHD (Rimm et al. (1996)). Soluble dietary fiber, in particular, has been shown clinically to reduce the need for insulin, (Landin et al. (1992)) improve glycemia (Aro et al. (1981)), and reduce serum LDL-cholesterol (Brown et al. (1999)). Its viscosity is proposed as an important mechanistic factor (Jenkins et al. (1978)). However, to date, there is no clearly effective composition or method for reducing blood glucose.

SUMMARY OF THE INVENTION

The present inventor has determined that the addition of high-viscosity fiber, in the form of a *konjac-mannan* mixture, or ginseng, or a composition comprising a *konjac-mannan* mixture and ginseng to a diet of an animal enhances conventional treatment outcomes, such as for diabetes and coronary heart disease, assessed primarily by total/HDL cholesterol, fructosamine, and sBP and secondarily by total, LDL, and HDL cholesterol; apolipoprotein A-1 (Apo A-1), B (Apo B) and their ratio; glucose; insulin; and systolic blood pressure (dBP).

Accordingly, in one aspect the present invention provides a composition of matter for reducing blood glucose comprising a *konjac-mannan* mixture. In another aspect of the invention, a sufficient amount of the *konjac-mannan* mixture, when given to an animal preferably at an appropriate time, reduces blood glucose in the animal, preferably postprandial blood glucose. Preferably the *konjac-mannan* mixture comprises *konjac-mannan* and a substance capable of increasing the viscosity of *konjac-mannan* from 50% to about 250% of *konjac-mannan* alone. More preferably the substance comprises about 5% to about 45% by weight of one or more such substances, preferably polysaccharides.

According to one embodiment a composition as just mentioned comprises as the one or more polysaccharides xanthan, carragenan, acetan, guar, or xyloglucana.

According to another embodiment a composition according to the invention comprises consitituents with the particle size larger than about 1,000 angstroms. In one aspect such a composition is used in controlling cholesterol levels, preferably lowering cholesterol levels.

Preferably, compositions according to the invention are formulated into a liquid, powder or formulated as part of a food. However, in another embodiment the compositions of the invention are formulated into pills, capsules and tablets According to another aspect the present invention provides a method for reducing blood glucose in an animal comprising administering to the animal a sufficient amount of a konjac-*mannan* mixture at an appropriate time in order to reduce bood glucose, preferably postprandial blood glucose, in the animal. Preferably the konjac-*mannan* mixture comprises *konjac-mannan* and a substance capable of increasing the viscosity of *konjac-mannan* to from about 50% to about 250% of *konjac-mannan* alone, preferably the substance comprises from about 5% to about 45% by weight of one or more polysaccharides, more preferably the one or more polysaccharides are selected from the group consisting of xanthan, carragenan, acetan, guar, or xyloglucana.

According to one embodiment of the method, the particle size of the constituents of a mixture of the invention are larger than about 1000 angstroms.

According to another embodiment of the invention, a mixture according to the invention is administered orally in an amount of about 1 to about 4 grams per day, preferably the mixture is administered either prior to a meal or during the meal.

According to yet another embodiment of the method of the invention the administration of a mixture according to the invention is by a liquid, a powder, or as a part of a food product. In another embodiment administration is by way of tablet, capsule or pill.

According to another aspect of the invention, there is provided a composition of matter for reducing blood glucose comprising ginseng in one aspect of the invention a sufficient amount of ginseng, when given to an animal at an appropriate time reduces blood glucose, preferably postprandial blood glucose, in the animal.

According to another aspect of the invention, there is provided composition of matter for reducing blood glucose comprising an extract of ginseng, preferably American ginseng, a sufficient amount of which when given to an animal at an appropriate time reduces blood glucose in the animal. According to any of the ginseng compositions, whether root or extract, the ginseng is comprised of a ratio of proto-panaxadiols (diols) relative to protopanaxatriols (triols) that is preferably greater than about 1.0, most preferably about 1.5 or greater and more preferably about 1.90 or greater. In another embodiment, the diol/triol ratio is about 2.4 or greater. In one embodiment, the composition is formulated into a liquid, powder or formulated as part of a food. In another embodiment the composition is formulated into tablets, capsules or pills.

According to another aspect of the present invention there is provided a method for reducing blood glucose in an animal comprising administering to the animal a sufficient amount of ginseng at an appropriate time in order to reduce blood glucose in the animal. In another aspect, there is provided a method for reducing blood glucose in an animal comprising administering to the animal a sufficient amount of an extract of ginseng at an appropriate time in order to reduce blood glucose in the animal. According to either of these latter mentioned methods, preferably the ginseng or extract is administered before a meal or with a meal, more preferably the administration before meal occurs from about 1 to about 180 minutes before the meal.

According to one embodiment of the method of the invention the amount of ginseng or extract of ginseng is at least about 1000 mg per administration. In another embodiment, the amount of ginseng administered is between 1-9 g, preferably 1-4 g and most preferably 1-3 g.

According to another embodiment of the method of the invention the ginseng comprises a ratio of diols/triols of greater than about 1.0, most preferably about 1.5 or greater and more preferably about 1.90 or greater. In another embodiment, the triols/diols ratio is about 2.4 or greater.

According to yet another embodiment of the method of the invention the composition is administered as a food, a powder, or a liquid. In another embodiment the composition is formulated into tablets, capsules or pills.

According to another aspect of the present invention there is provided a composition of matter for reducing blood glucose comprising a *konjac-mannan* mixture of the invention and ginseng. In one embodiment of the invention a sufficient amount of *konjac-mannan* and ginseng which when given to an animal at an appropriate time reduces blood glucose in the animal. Preferably the *konjac-mannan* mixture comprises *konjac-mannan* and a substance capable of increasing the viscosity of *Konjac-mannan* from 50% to about 250% of *konjac-mannan* alone. Preferably the substance comprises about 10% to about 40% or one or more polysaccharides. More preferably the one or more polysaccharides are xanthan, carragenan, acetan, guar, or xyloglucana.

According to one embodiment according to this aspect of the invention the particle size of constituents within the mixture is larger than about 1,000 angstroms.

According to another embodiment according to this aspect of the invention the American ginseng is comprised of a ratio of diols/triols of greater than about 1.0, most preferably about 1.5 or greater and more preferably about 1.90 or greater. In another embodiment, the diol/triol ratio is about 2.4 or greater. According to yet another embodiment according to this aspect of the invention the composition is formulated into a liquid, powder or formulated as part of a food.

According to another embodiment, the ginseng used in the compositions and methods fo the invention can be any ginseng or extract thereof, for instance American, Asian, Chinese or other ginseng known in the art. In another embodiment, the ginseng is preferably American ginseng. In yet another embodiment of the invention, the ginseng or extract thereof has a diol/triol ratio of about 1.0, most preferably about 1.5 or greater and more preferably about 1.90 or greater. In another embodiment, the diol/triol ratio is about 2.4 or greater.

In another embodiment, the invention provides a method for determining whether a ginseng or extract thereof would be useful in controlling, modulating or lowering blood glucose, preferably postprandial blood glucose, by determining the diol/triol ratio of the ginseng or extract and selected for one that has a diol/triol ratio of about 1.5 or greater. The selected extract can then be optionally tested for such activity using the traditional tests and assays described herein or known in the art. In another embodiment, the selected ginseng can also be tested and selected for insulin, lipid profile, cholesterol and blood pressure control, modulation or decrease. In yet another embodiment the selected ginseng can be tested and selected for effectiveness in the treatment of diabetes and/or cardiovascular disease.

According to another aspect of the present invention the compositions and methods of the invention can be applied to the treatment of long term diabetes, heart disease, and syndrome X. In addition the compositions and methods of the invention provide methods for increasing insulin sensitivity in an animal and of treating type 2 diabetes as well as for reducing systolic blood pressure or blood cholesterol and other lipids and apolipoproteins The details of the preferred embodiment of the present invention are set forth in the accompanying drawings and the description below. Once the details of the invention are known, numerous additional innovations and changes will become obvious to one skilled in the art.

BRIEF DESCRIPTION OF THE DRAWINGS

The invention will be better understood with reference to the drawings is in which:

FIG. 4 illustrates the effect of konjac mannan versus placebo on blood glucose levels as described in Example 10. FIG. 4A is a linear graph illustrating glucose response to a test breakfast before 3-week treatment and FIG. 4B is a linear graph illustrating glucose response to a test breakfast after the 3 week treatment. FIG. 4C is a bar graph illustrating glucose area under the curve (AUC) before and after the 3-week treatment.

FIG. 5 illustrates the effect of *konjac* mannan versus placebo on blood insulin levels as described in Example 10. FIG. 5A is a linear graph illustrating insulin response to a test breakfast before 3-week treatment and FIG. 5B is a linear graph illustrating insulin response to a test breakfast after the 3 week treatment. FIG. 5C is a bar graph illustrating insulin area under the curve (AUC) before and after the 3-week treatment.

FIG. 6 illustrates the effect of highly refined *konjac* mannan versus the *konjac* mixture of the invention as described in Example 11. FIG. 6B is a linear graph illustrating incremental blood glucose levels.

FIG. 7 is a linear graph illustrating the results of Example 12 for the effect of *konjac* mannan, American ginseng and both *konjac* mannan and American ginseng on systolic blood pressure.

FIG. 8 illustrated the effect of *konjac* mannan and ginseng treatment versus the separate treatments on blood glucose. FIGS. 8A and B are linear graphs illustrating blood glucose levels versus time and changes therein as described in Example 13.

DETAILED DESCRIPTION OF PREFERRED EMBODIMENTS OF THE INVENTION

Figure 1:
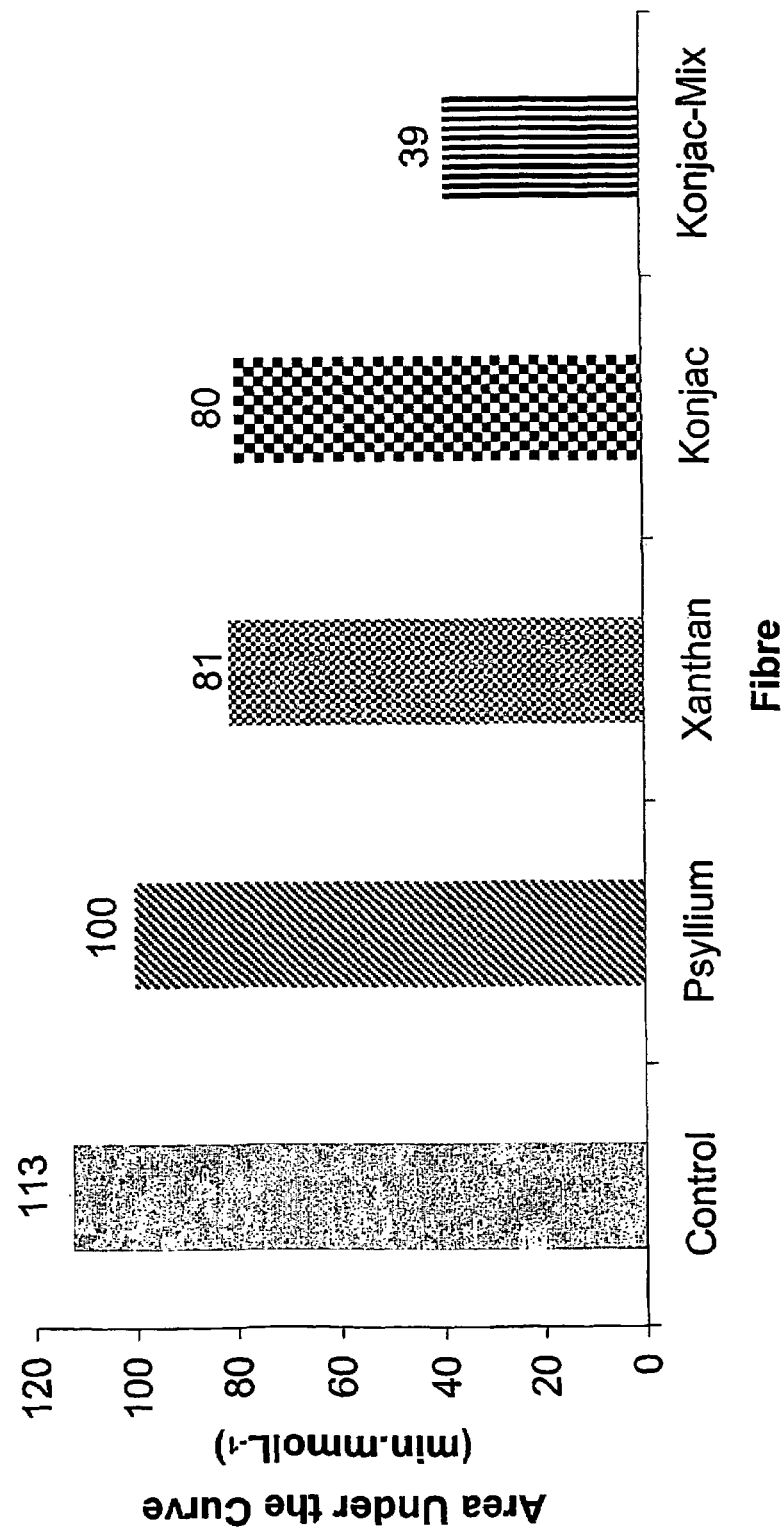
FIG. 1 is a histogram illustrating the effect of various fibres including *Konjac* mannan alone on glucose response in individuals in eleven individuals in comparison with a *Konjac-mannan* mixture of the present invention.

As described above, the present invention is related to compositions and methods for reducing blood glucose. In particular, the present inventor has found that a *konjac* mannan mixture, a ginseng composition, or a composition comprising *konjac* mannan and ginseng are effective in the reduction of blood glucose. In another embodiment, the compositions of the invention are effective in controlling or modulating the lipid profile of an animal, blood pressure and insulin levels. The compositions fo the invention A enhances conventional treatment outcomes, such as for diabetes and coronary heart disease, assessed primarily by total/HDL cholesterol, fructosamine, and sBP and secondarily by total, LDL, and HDL cholesterol; apolipoprotein A-1 (Apo A-1), B (Apo B) and their ratio; glucose; insulin; and systolic blood pressure (dBP).

As used herein "about" when referring to a value includes amounts that within the scope of scientific certainty or uncertainty. Such amounts would include amounts that are effectively equivalent to the values stated. "About" when used in relation to diolitriol ratios means plus or minus 10% of the value.

As used herein "animal" means any member of the animal kingdom including preferably humans.

As used herein "postprandial" means after any food intake.

As used herein "sufficient amount" or "effective amount" means an amount of a composition, substance or reactant to give an observable result, including desired results.

As used herein "appropriate time" means at a time at which administration of a substance or composition provides an observable result.

As used herein "prior to a meal" means at any time after a meal and before a subsequent meal.

As used herein "during a meal" means at any time after the commencement of consumption of one or more pieces of food by an animal, and can be coincident with commencement, and before the end of consumption of all food consumed by the animal, at one sitting or occasion and can be coincident with completion of consumption or immediately thereafter.

As used herein "a food" means any substance or composition of substances or compounds which are consumed by an animal, preferably for some nutritional value.

As used herein "a meal" means the consumption of one or more morsels or pieces of a food in a sitting where a sitting is the time taken to consume the one or more morsels or pieces of a food.

As used herein, "diolittriol ratio(s)" or "diols/triols" refers to protopanaxadiols (diols) relative to protopanaxatriols (triols).

Konjac -Mannan

Konjac (*Amorphophalus Konjac C. Koch*) is a perennial plant belonging to the family Araceae. "Konnyaku", which is made from the tuber of this plant, has been used traditionally for food in Japan for several hundred years. The predominant component of edible konnyaku is a glucomannan called *konjac -mannan* (KJM). Edible konnyaku is made from the *konjac* flour, which is obtained from the dried tuber of this plant. KJM flour is obtained by grinding the tuber root of the *Amorphophallus Konjac C. Koch*. plant and is traditionally used as a food and remedy in the Far East. In addition to previous findings (Vuksan et al. (1999)), other findings have shown it to improve cholesterol levels (Arvill et al. (1995)), hypertension, and glycemia (Doi et al. (1979); Shima et al. (1982)).

*Konjac-mannan* was chosen as the fibre because it represents a polysaccharide with one of the highest viscosities (Kiriyama et al. (1972)). The physiologically active component is a high molecular weight glucomannan polymer, which, when taken as a supplement, has been shown to have effects in lowering lipids (Arvill et al. (1995); Terasawa et al. (1979); Venter et al. (1987)), systolic blood pressure (sBP) (Arvill et al. (1995)), and glycemia (Doi et al. (1979); Shima et al. (1982)).

Several techniques are known in the art for separating *konjac -mannan* from *konjac* flour. In one, *konjac* flour is boiled in water, treated with Fehling's solution to convert the mannan to its copper complex, and the latter is decomposed again into the mannan after purification, as disclosed in J. Agr. Chem. Soc. Japan, 6, 991-995 (1930). In another, *konjac* flour is extracted with water, impurities are removed by precipitating with ethanol and redissolving the precipitate in water several times, and drying the precipitate finally obtained to obtain pure *konjac-mannan*, as disclosed in Bull. Chem. Soc. Japan, 49, 298-322 (1927). Water-soluble *konjac -mannan* capable of undergoing gelation when heated in an aqueous alkaline solution may be used as described in U.S. Pat. No. 3,973,008. Briefly it is obtained by extracting the ground tuber of the *konjac* plant with water, separating insoluble matter, dialyzing the solids-free liquid against water and then lyophilizing the dialyzed liquid to remove water. A person skilled in the art would be familiar with suitable *konjac-mannan* preparation protocols for use herein. All such preparation methods are intended to be encompassed within the scope of the present invention.

The present invention provides an improved *konjac* mannan composition.

The *konjac-mannan* composition or mixture of the invention preferably comprises *konjac-mannan* and a substance that can increase the viscosity of the *konjac-mannan* by 50-250%. Accordingly, in one aspect the present invention provides a composition of matter for reducing blood glucose comprising a *konjac-mannan* mixture. In another aspect of the invention, a sufficient amount of the *konjac-mannan* mixture, when given to an animal preferably at an appropriate time, reduces blood glucose in the animal, preferably postprandial blood glucose. Preferably the *konjac-mannan* mixture comprises *konjac-mannan* and a substance capable of increasing the viscosity of *konjac-mannan* from 50% to about 250% of *konjac-mannan* alone. More preferably the substance comprises about 5% to about 45% by weight of one or more such substances, preferably polysaccharides.

According to one embodiment a composition as just mentioned comprises as the one or more polysaccharides xanthan, carragenan, acetan, guar, or xyloglucana.

According to another embodiment a composition according to the invention comprises consitituents with the particle size larger than about 1,000 angstroms. In one aspect such a composition is used in controlling cholesterol levels, preferably lowering cholesterol levels.

Preferably, compositions according to the invention are formulated into a liquid, powder or formulated as part of a food. However, in another embodiment the compositions of the invention are formulated into pills, capsules and tablets According to another aspect the present invention provides a method for reducing blood glucose in an animal comprising administering to the animal a sufficient amount of a *konjac-mannan* mixture at an appropriate time in order to reduce bood glucose, preferably postprandial blood glucose, in the animal. Preferably the *konjac-mannan* mixture comprises *konjac-mannan* and a substance capable of increasing the viscosity of *konjac-mannan* to from about 50% to about 250% of *konjac-mannan* alone, preferably the substance comprises from about 5% to about 45% by weight of one or more polysaccharides, more preferably the one or more polysaccharides are selected from the group consisting of xanthan, carragenan, acetan, guar, or xyloglucana.

According to one embodiment of the method, the particle size of the constituents of a mixture of the invention are larger than about 1000 angstroms.

According to another embodiment of the invention, a mixture according to the invention is administered orally in an amount of about 1 to about 4 grams per day, preferably the mixture is administered either prior to a meal or during the meal.

According to yet another embodiment of the method of the invention the administration of a mixture according to the invention is by a liquid, a powder, or as a part of a food product. In another embodiment administration is by way of tablet, capsule or pill.

Ginseng

A main ingredient of the ginseng is saponin. As the saponin included in this ginseng there have been known twelve kinds of ginsenside-Ro, -Ra, -Rb1, -Rb2, -Rc, -Rd, -Re, -Rf, -Rg1, -Rg2, -Rg3, -Rh. These are the one (ginsenside-Rb1, -Rb2, -Rc) containing sapogenen and protopanaxadiol, and the one (ginsenside-Re, Rf, -Rg1, -Rg2) containing sapogenen and protopanaxatriol. The main saponin in the crude drug is ginsenside-Rb1, -Rb2, -Rc, -Rg1. The ginsenside-Ro is the same as chikusetsusaponin V, and the ginsenside-Rb1 is the same as saponin D.

Besides these, the ginseng contains essential oil of 0.05%, .beta.-elemene, panacene ($C_{15}H_{24}$) and panaxynol as polyacetylene compound and further contains choline, vitamin B complex, fatty acid etc.

There are known to be at least seven different types of ginseng and in the present disclosure a prefered form is American ginseng. There are many types of ginseng, American, Asian, and others known in the art, and various subspecies thereof. Not all have the same compositions or therapeutic effects, even within the same species. Effectiveness can also depend on the method of preparation of ginseng composition.

According to another embodiment, the ginseng used in the compositions and methods of the invention can be any ginseng or extract thereof, for instance American, Asian, Chinese or other ginseng known in the art. In another embodiment, the ginseng is preferably American ginseng. In yet another embodiment of the invention, the ginseng or extract thereof has a diol/triol ratio of about 1.0, most preferably about 1.5 or greater and more preferably about 1.90 or greater. In another embodiment, the diol/triol ratio is about 2.4 or greater.

According to one embodiment of the method of the invention the amount of ginseng or extract of ginseng is at least about 1000 mg per administration. In another embodiment, the amount of ginseng administered is between 1-9 g, preferably 1-4 g and most preferably 1-3 g.

In another embodiment, the invention provides a method for determining whether a ginseng or extract thereof would be useful in controlling, modulating or lowering blood glucose, preferably postprandial blood glucose, by determining the diol/triol ratio of the ginseng or extract and selected for one that has a diol/triol ratio of about 1.5 or greater. The selected extract can then be optionally tested for such activity using the traditional tests and assays described herein or known in the art. In another embodiment, the selected ginseng can also be tested and selected for insulin, lipid profile, cholesterol and blood pressure control, modulation or decrease. In yet another embodiment the selected ginseng can be tested and selected for effectiveness in the treatment of diabetes and/or cardiovascular disease.

Ginseng, preferably American Ginseng (*Panax quinquefolium L.*) reduces postprandial blood glucose in nondiabetic and people with diabetes. Preferably at least 1000 mg of ginseng, preferably American ginseng is administered together or before the meal (up to 180 min) to see an effect on the postprandial blood glucose responses to a test meal. While in nondiabetic it is important to take ginseng before meal, in type 2 diabetes, the effect is seen irrespective of time of consumption (together with meal or up to 180 min before meal).

Ginseng, such as American ginseng with a profile of diovtriol ratio of greater than about 1.0, most preferably 1.5 or greater and more preferably 1.90 or greater. In another embodiment, the triols/diols ratio is about 2.4 or greater. In one embodiment the composition may be administered in the same manner as described above to produce glucose lowering effects. Ginseng with a particular ginsenosides profile may have an effect on increased secretion of the first phase insulin, similar to conventional diabetic drugs.

Ginseng roots was selected by chemical composition analysis using HPLC. If ginseng extract is used, it can be prepared by usaly extraction procedure, by using water to alcohol solution in ratio between 40% to 80% of water, with the rest being alcohol. Other ginseng, and extract preparation procedures are known in the art.

The present invention shows for the first time, that ginseng (root or extract) with protopanaxadiols to protopanaxatriols ratio higher than about 1.0, most preferable 1.5, lowers the postprandial glycemic response in both healthy and diabetic individuals and in the long term reduces serum lipids and blood pressure and thus improves diabetes control. Not intending to be bound by a particular theory, studies conducted by the present inventors indicate that ginseng may potentate insulin secretion potentially through a modulation of autocoid metabolism linked to nitric oxide production. However, gut mediated hormone effects may play part in the mechanism of action of AM but this area has not yet been explored.

*Konjac Mannan* and Ginseng

The invention also comprises the administration of both ginseng (such as American Ginseng (*Panax quinquefolium L.*) and *konjac-mannan*, jointly. A combination of selected ginseng, such as American Ginseng (*Panax quinquefolium L.*) and *Konjac-Mannan* fiber (*Amorpophallus Konjac k*) act jointly to reduce postprandial blood glucose in people with Type 2 diabetes more then each individual material. The efficacy is not attainable by either treatment. The ginseng can be any ginseng or formulation thereof, preferably as described above, more preferably that has a diol/triol ratio of greater than about 1.5 or more. The *konjac-mannan* is preferably the *konjac-mannan* mix as described above. The *konjac-mannan* and ginseng can be prepared and administered in separate compositions or can be formulated into one composition.

While not wishing to be bound by any particular theory, the possible mechanism of action for the hypoglycaemic effect of *konjac*/ginseng is to increase insulin secretion/sensitivity, and together with *konjac -mannan's* ability to slow nutrient absorption and also improve insulin sensitivity these combined effects result in lower prolonged elevation of postprandial blood glucose and have applications in prevention and treatment of diabetes and heart disease. Thus there are two products, operating through different pathways, that significantly reduce key risk factors for diabetes and cardiovascular disease.

Compositions

For the purposes of administration by means other than incorporation within a food, the compositions described herein can be prepared by per se known methods for the preparation of pharmaceutically acceptable compositions which can be administered to subjects, such that an effective quantity of the composition of the invention is combined in a mixture with a pharmaceutically acceptable vehicle, thereby allowing for the administration of a sufficient amount of the composition. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

One would appreciate that the effective or sufficient amount of a composition of the invention can vary depending on the individual, such as sex, age, and weight of the individual, and/or severity of a condition, such as diabetes. It may also in certain cases vary on the time of administration, i.e. post or pre meal and time it takes for the substance to clear or be metabolized by the body. It may also vary depending on whether the compositions are administered separately or with another substance that may modulate the effectiveness of the composition. For instance the effective amount of *konjac-mannan* may vary depending on whether it is administered alone or in conjunction with a ginseng or another substance that may act synergistically with it. It may also vary depending on the concentration and mode of preparation of the *konjac-mannan* being administered. The above similarly applied to the administration of ginseng.

Such compositions in one aspect are administered orally, such as by liquid, powder or formulated as part of a food, such as a biscuit. It could be administered in the form of pills, capsules and tablets. Other forms of administration may also be suitable.

Such composition can be used in the modulation or control, preferably decrease, of blood glucose, preferably postprandial blood glucose. In another aspect the compositions of the invention can also be used to modulate or control insulin levels in an animal, preferably decrease such levels. The compositions of the invention can also be used to modulate a lipid profile of a patient in need thereof. They can also be used to modulate blood pressure, preferably to lower blood pressure. In a preferred embodiment the invention can be used in the treatment of animals, preferably humans, in need of controlling their glucose levels, such as in the management and treatment of diabetes. In another embodiment, the compositions of the invention can be used in the management and treatment of cardiovascular disease and associated conditions, such as high blood pressure, high cholesterol level. In another embodiment, the compositions of the invention, especially the ginseng compositions, can be used to modulate or control nitric oxide levels in an animal.

The following non-limiting examples are illustrative of the present invention:

EXAMPLES

General Methods for Examples 1-4

Subjects

Eleven diabetic patients (5 men, 6 women) gave written informed consent to participate in the present study that was approved by the Human Ethic Committees of St. Michael's Hospital and the University of Toronto. All had hyperlipidemia, hypertension, and type 2 diabetes (mean serum C-peptide 701±351 pmol/L), with a minimum of three years since the onset of all three conditions. They were taking medications to control each of the three risk factors, consuming a National Cholesterol Education Program (NCEP) Step 2 diet Executive Summary of the Third Report of the National Cholesterol Education Program (NCEP) Expert Panel on Detection, Evaluation, and Treatment of High Blood Cholesterol in Adults. JAMA;285:2486-2497,2001, not smoking, nor taking alcohol, and leading sedentary lifestyles at recruitment. Two participants had a history of atherosclerotic heart disease, but none had evidence of recent myocardial infarction, unstable angina, or congestive heart failure. Exclusion criteria were a family history of premature CHD, hypothyroidism, renal, hepatic, or gastrointestinal disease. Table 1 provides baseline demographic, anthropometric and clinical characteristics of the study participants.

Study Design

The study employed a double-blind, placebo-controlled, cross-over design, where all subjects were maintained on the same dosage of their medications throughout. The study began with an 8 week baseline period over which participants followed an NCEP Step 2 ad libitum diet: Executive Summary of the Third Report of the National Cholesterol Education Program (NCEP) Expert Panel on Detection, Evaluation, and Treatment of High Blood Cholesterol in Adults. JAMA;285:2486-2497,2001, documented by three non-consecutive days of food records every two weeks. This was followed by the experimental phase of the study that consisted of two successive 3 week treatment periods, separated by a two week washout interval over which another three day food record was obtained. During the first treatment period, subjects were randomly assigned to either the KJM+ (Step 2 metabolically controlled diet enriched with fiber) or the control treatment (the same diet enriched with wheat bran [WB] fiber). For the second treatment period, the subjects were crossed-over. The study began with 5 subjects taking the KJM+ treatment and 6 the control.

Diet

Both treatments consisted of a three-day rotating Step 2 diet with three meals per day provided under metabolic conditions. All foods were pre-weighed, packaged and couriered to participants for consumption at home or at work. The mean macronutrient profile conformed with a Step 2 diet. Energy intakes for weight maintenance were provided according to Lipid Research Clinics Tables with adjustment for physical activity (The Lipid Research Clinics Population Studies Data Book. Vol. 2. The prevalence study-nutrient intake. Washington DC: Government printing office (NIH publication no. 82-2014) (1982)). Total dietary fiber was administrated at 2 g/412 kJ (100 kcal), with a mean daily intake according to energy intake ranging from 24 g to a plateau of 50 g for those consuming 2500 Kcal per day or more. The actual diet consumed is presented in Table 2.

The two treatments differed only in the type of fiber. On the KJM+ treatment, participants received KJM+ enriched biscuits, whereas on the control treatment they received an equal quantity of wheat bran (placebo) biscuits. Subjects were instructed to take biscuits together with an 8 oz beverage, 3 times daily as a snack, including once at bed-time. Both were produced and provided by Dicofarm S.p.A, Roma, Italy, (commercially available in Italy as "Dicoman®" biscuits). They had similar nutrient profiles (Table 2) and were indistinguishable in taste and appearance. KJM+ biscuits contained approximately 15% KJM flour of which 69% was the active high viscosity glucomannan, 15% other polysaccharides, and 16% excipients by weight. The KJM flour mix used in the biscuits comprised in % by weight: 69% KJM, 21% xanthan and 10% caragenan. Because KJM flour comprised half (1 g/412 kJ [100 kcal]) of the total fibre on the KJM+ treatment, approximately 0.7 g/412 kJ (100 kcal) was glucomannan. Wheat bran biscuits, in contrast, had a lower proportion of fiber than KJM+ biscuits (Table 3). Approximately 14 g/day of wheat bran fibre derived from standardized American Association of Cereal Chemist hard red wheat bran was, therefore, added to the control (WB) diet to compensate for these fiber differences.

Any food from the metabolic diet together with study biscuits not consumed was brought to the clinic for weighing to measure compliance. Dietary changes found to occur during the first three-week treatment period were duplicated prior to food delivery for the second treatment period for each participant.

Laboratory Methods

Serum blood samples were immediately separated and stored in four aliquots at −70° C. after collection. They were thawed at the end of the study for analysis of total cholesterol, HDL, and triglycerides (TRIG) measured enzymatically (McNamara et al. (1987); Warnick et al. (1982)). LDL content was estimated by the formula of Friedewald et al. (Friedewald et al. (1972)). Apolipoprotein (Apo) A1 and B were determined by rocket immunoelectrophoresis (Fruchart et al. (1982)). Fasting blood glucose was analyzed by a hexokinase method using a Cobas Mira Autoanalyzer (Roche Diagnostic, Mississauga, Canada). Serum fructosamine was analyzed in triplicate using the Cobas Fara II (Lloyd et al. (1984)) and plasma insulin in duplicate by radioimmunoassay with reagent from ICN Biomedicals, Inc. (Horsham, Pa.) (Livesey et al. (1980)). Finally, C-peptide was determined by radioimmunoassay (Kuzuya et al. (1976)).

Physical measurements were obtained by standard techniques. Blood pressure was taken and expressed as the mean of three measurements to the nearest 2 mm Hg on both arms. Fasting body weight was determined using a beam scale in light clothing, with an emptied bladder and in bare feet. Waist and hip circumferences were measured by soft non-stretchable tape on the narrowest and widest parts of the trunk.

Energy and nutrient analysis of the diets was calculated using US Department of Agriculture data (The Agriculture Research Services. *Composition of Foods, Agriculture Handbook No.* 8. Washington, DC, US Department of Agriculture, 1992). The nutrient composition of the treatment biscuits was analyzed, using the Prosky method to determine fiber content (Prosky et al. (1985)

Statistical Analyses

Results are expressed as mean±SEM, except for age, anthropometric measurements and nutrient intake (mean±SD). Data were analyzed by the Statistical Analysis System (SAS) (SAS Institute Inc.: *SAS/STAT User's guide*. Version 6, $4^{th}$ ed. Cary N.C.: SAS Institute Inc. 1989)). Differences in serum lipids, apolipoproteins, glycemia, blood pressure and body weight between the beginning (week-0) and end (week-3) of each treatment (control and KJM+) were assessed by two-tailed Student's t-test for paired data (PROC UNIVARIATE). Analysis of covariance (ANCOVA) with the facility of General Linear Model procedure (PROC GLM) was used to test for differences in these same parameters between the two treatments. Adjustment for multiple comparisons was made by the Bonferroni-Hochberg procedure (Hochberg (1988)) for primary (fructosamine, total/HDL cholesterol ratio, and sBP) and secondary (body weight; total, LDL and HDL cholesterol; Apo A-1; Apo B; Apo A-1/B ratio; glucose; insulin; and dBP) endpoints separately. P-values for each endpoint were ordered sequentially and contrasted with the corresponding adjusted comparison wise critical alpha ($\alpha$) levels. Null hypotheses were rejected only if the p-values were less than their corresponding $\alpha$-values (Hochberg (1988)). Control of individual variation from the repeat measures aspect of the design was addressed by incorporating the random subject effect as well as the starting measurement. Diet, sex, and phase effects were also incorporated in this model. To test for confounding effects of body weight on study parameters, Pearson correlations were performed (PROC CORR procedure).

Example 1

All participants followed the experimental protocol with little difficulty. According to three-day food records collected over the baseline and washout periods, subjects ate their usual low-fat (<25% energy) and high-fiber (>27 g per day) diets (Table 3). In addition, during the treatment periods, returned food and biscuits from metabolic diets indicated that subjects consumed an average of 93% and 95% of diet calories prescribed on the KJM+ and control (WB) treatments respectively and 88% (137 g/day) KJM+ test and 91% (142 g/day) WB placebo biscuits. Consumption patterns translated into an insignificant decrease in body weight during both treatment periods (Table 4). There was no correlation between changes in weight and serum lipids, glucose or blood pressure (data not shown). The only side effect experienced was a transient complaint of flatulence and soft stools reported by 37% and 24% of participants during the KJM+ and the control (WB) treatments respectively, but none refused to continue the study.

Example 2

Blood lipids were improved during KJM+ treatment compared to control (Table 4). The primary lipid endpoint, total/HDL cholesterol, decreased significantly by 5.7±2.3% (P=0.034, $\alpha$=0.05) during the KJM+ treatment compared to an insignificant increase of 4.7±4.4% (P=0.316, $\alpha$=0.017) on control. The resultant between-treatment decrease of 10±4.0% on the KJM+ treatment was significant (P=0.028, $\alpha$=0.05). The secondary endpoints of total and LDL cholesterol also fell significantly by 16±2.7% (P=0.001, $\alpha$=0.005), 25±3.9% (P=0.001, $\alpha$=0.005), during KJM+ treatment compared to 4.9±3.7% (P=0.20, $\alpha$=0.006), and 4.8±5.9% (P=0.45, $\alpha$=0.008) on control. Resultant between-treatment differences of 11±4.2% (P=0.025, $\alpha$=0.005) and 19±6.8% (P=0.033, $\alpha$=0.006), were insignificant, however, after correction by the Bonferroni-Hochberg procedure. The combined fall in total cholesterol and LDL on the KJM+ treatment indicated reclassification of the lipid status of 6 of the 11 subjects from elevated to normal cholesterolemia (<5.2 mmol/L) (2). Values for LDL, however, were derived from only 9 subjects, because two of the 11 participants had serum triglycerides levels over 4.5 mmo/L, not allowing for calculation by the Friedewald equation.

Similar results were observed for Apo B and the Apo B/A-1 ratio. During KJM+ treatment both fell significantly by 14±3.4% (P=0.002, $\alpha$=0.006) and 8.6±9.3% (P=0.004, $\alpha$=0.007), compared to 3.0±5.0% (P=0.57, $\alpha$=0.013) and 3.0±4.8% (P=0.55, $\alpha$=0.01) on control respectively. These changes, however, resulted in an insignificant between-treatment difference of 11±4.3% (P=0.025, $\alpha$=0.005) and 5.6±4.5% (P=0.24, $\alpha$=0.008), after correction by the Bonferroni-Hochberg procedure.

In contrast, such effects were not seen on HDL, Apo A-1, or triglycerides. During KJM+ and control treatments, HDL and Apo A-1 decreased insignificantly, for insignificant between treatment changes. Similarly, during both treatments, triglycerides increased insignificantly, with no significant difference between treatments.

Example 3

Improvements in glycemic control were observed on the KJM+ treatment compared to control (Table 4). The primary glycemic endpoint, serum fructosamine, was reduced insignificantly during both the KJM+ and control treatments by 6.1±2.4% (P=0.03, $\alpha$=0.025), and 0.5±1.4% (P=0.751, $\alpha$=0.05) respectively, after correction by the Bonferroni procedure. The resultant between treatment decrease of 5.7±1.7% on KJM+ was nevertheless significant (P=0.007, $\alpha$=0.017). No significant differences between treatment regimes were seen for the secondary endpoints of insulin or glucose, although during the KJM+ treatment, fasting glycemia fell significantly by 11±3.0% (P=0.004, $\alpha$=0.008) compared to 1.5±6.1% (P=0.804, $\alpha$=0.013) on control.

Example 4

An improvement in blood pressure was also observed on the KJM+ treatment compared to control (Table 4). The primary blood pressure endpoint, sBP, decreased significantly on KJM+ supplementation by 5.5±1.4% (P=0.003, α=0.017), compared to 1.4±2.7% (P=0.62, α=0.03) on control, producing a significant between-treatment difference of 6.9±2.5% (P=0.021, α=0.025) or 9.4±3 mm Hg. During both treatments, diastolic blood pressure (dBP), however, remained virtually unchanged with no significant difference between treatments. The result was a reclassification in sBP status from moderately high to normotensive (<135 mmHg) in 5 of 11 subjects after the KJM+ treatment.

Discussion of Examples 1-4

Examples 1-4 illustrate that the addition of 0.7 g/412 kJ (100 kcal) of high viscosity glucomannan (KJM mix) in biscuit form to conventional CHD treatment (a low saturated fat diet combined with drug therapy) improved metabolic control beyond the effect of conventional treatment alone in high-risk individuals with type 2 diabetes. Amelioration in three major CHD risk factors—hyperglycemia, hypertension, and hyperlipidemia—relative to a matched placebo control treatment as measured by the primary endpoints fructosamine, sBP, and total/HDL cholesterol respectively was observed. Differences between secondary glycemic, blood pressure, and lipid endpoints were insignificant after adjustment for multiple comparisons by the Bonferroni-Hochberg procedure. With greater power derived from a larger sample size, significance might have been achieved in these cases.

To achieve similar metabolic benefits, the recent dietary recommendations of the American Diabetes Association have changed their emphasis from encouraging carbohydrate and less processed fiber foods to increased consumption of monounsaturated fat (American Diabetes Association (ADA): Nutrition Recommendations and principles for people with diabetes mellitus. *Diabetes care* 22:S42-S43, 1999). Their reasoning is that fiber has only very modest effects on LDL cholesterol and does nothing to raise HDL cholesterol levels. Nevertheless, the diet usually prescribed for the management of CHD risk factors in people with diabetes resembles an NCEP Step 1 or 2 diet. The recommendations for these diets are as follows: for Step 1, of total calories <30% from total, <10% from saturated, and <10% from polyunsaturated, with <300 mg/day of cholesterol and for Step 2 the same except <7% of calories from saturated fat with <200 mg/day of cholesterol. In the two well-controlled clinical studies in this area, limitations of the diets are evident. Hunninghake et al., following hypercholesterolemic subjects on a Step 2 diet for three months, found that LDL was reduced by only 5% (Hunninghake et al. (1993)). Schaefer and colleagues found a reduction in LDL in subjects provided a Step 2 diet on a metabolic basis to be as much as 17%, but with adverse effects on other lipid parameters and no effect on total/HDL cholesterol ratio (Schaefer et al. (1995)). A high inter-subject variability in LDL reductions was also noticed. The present results, however, showed that KJM+ treatment resulted in an improvement in lipid ratios. The suggestion is that a Step 2 diet supplemented with KJM+ may confer additional benefits over this diet alone.

Lipids

Improvements in blood lipid control have previously been shown when Step 2 diets were supplemented with soluble fibre from different dietary sources (Jenkins et al. (1993)) or fibre supplements (Anderson et al. (1986); Olson et al. (1997)). While such studies have reported reduced total and LDL concentrations, few, as has been the case for NCEP diets, have reported improved lipoprotein ratios. Out of the three lipid trials that used KJM+ (Arvill et al. (1995); Terasawa et al. (1979); Venter et al. (1987)) the former two did not show a significant change in these ratios. In contrast, Venter and coworkers (Venter et al. (1987)) found 4.5 g/day glucomanan significantly improved both LDL and the LDL/HDL ratio in 18 hypercholesterolemic subjects. The present examples showed a more significant 10±4.0% decrease in the total/HDL ratio were noticed on the KJM+ treatment compared to control. The mechanism by which the KJM+ supplemented biscuits had this lipid lowering effect is not clear. While not wishing to be bound by any particular theory, possibilities include an inhibition of cholesterol absorption in the jejunum (Ebihara et al. (1989)) and bile acid absorption in the ileum (Kiriyama et al. (1974)) or less postprandial stimulation of HMG CoA reductase (Jenkins et al. (1993)). Other options include the generation of short chain fatty acids by colonic microflora, predominantly propionate, which may decrease hepatic cholesterol synthesis (Venter et al. (1990)).

Glycemic Control

Improvements in diabetes control after soluble fibre supplementation have been shown (Morgan et al. (1990)). KJM, in particular, has been shown to have a beneficial effect following both acute (Shima et al. (1982)) and long-term (Doi et al. (1979); Shima et al. (1982)) administration. In the present invention KJM+ treatment compared to control, a 5.7±1.7% reduction was observed in serum fructosamine, a short-term marker of diabetes control, with no effect on either fasting glucose or insulin concentrations. These results were not altered by excluding four subjects treated with insulin. An effect of the gel forming KJM+ on digestion may explain this finding. It has been suggested that decreases in glucose and insulin levels after the consumption of water-soluble fibers are related to slower rates of food absorption in the small intestine associated with increased viscosity (Ebihara et al. (1981)). KJM has been shown to have very high viscosity, approximately five times higher than guar gum (Ebihara et al. (1981)) and considerably more than pectin (Venter et al. (1987)). Consequently, in some studies it has been given at half the dosage relative to these other fibers (Ebihara et al. (1981)). The present inventors have further increased the viscosity of KJM by the addition of polysaccharides such xanthan, caragenan, acetan, guar or xyloglucena.

Blood Pressure

Finally, although few studies have demonstrated an effect of fibre on blood pressure, significant reductions both in sBP and dBP have been reported after consumption of guar granulates (Landin et al. (1992)) and soluble dietary fibre supplements (Alison et al. (1992)). The same effect has been shown for KJM, but only on sBP (Arvill et al. (1995)). This last finding agrees with the results set out in the present examples, in which KJM treatment significantly reduced sBP by 6.9% compared to control but did not affect dPB. The commonly recommended oat bran, in contrast, has been shown to affect neither systolic nor diastolic blood pressure (Swain et al. (1990)). While not wishing to be bound by any particular theory, a possible mechanism for the blood pressure lowering effect of soluble fibers may involve increased insulin sensitivity (Anderson et al. (1986)), which may reduce blood pressure by influencing sodium absorption in the distal tubule, increasing sympathetic nervous system activity and peripheral vascular resistance (Modan et al. (1985)).

The effect of KJM+ fibre supplements on the three CHD risk factors persist even in subjects who are taking conventional drug therapy concurrently. Consistent with the findings set forth in the examples, a combination of fiber and drugs has been shown to be more effective clinically than the drug given alone in improving metabolic control. Toumilehto and coworkers (Tuomilehto et al. (1989)) found that the viscous soluble fiber guar gum and gemfibrozil administered together reduced total cholesterol and LDL/HDL ratio significantly more than gemfibrozil and placebo. Elsewhere this same effect has been noticed for blood glucose and blood pressure. A significant reduction was found in postprandial blood glucose after consumption of sulfonylyurea (glibenclamide) and glucomannan with a test meal compared to sulfonylyurea alone with the same test meal (Shima et al. (1983)). Similarly, a significant decrease in diastolic blood pressure was noticed after administration of guar gum compared to placebo in patients receiving drug treatment for hypertension (Uuistupa et al. (1984)). Together these findings suggest that highly viscous soluble fibre may augment or potentiate the effect of drugs.

In conclusion, the application of KJM+ supplementation in the high-risk diabetic study group of the examples demonstrated simultaneous improvement in all three diet-modifiable risk factors, indicating a reduction in overall CHD risk (Jenkins et al. (1995)). One of the benefits is that KJM+ supplemented therapy may lower required drug dosages and improve overall cost-effectiveness and acceptability of treatment. Although it is agreed that food should be the normal way to achieve an adequate fiber intake, fiber supplemented foods have advantages in the treatment of individuals at high risk for CHD and represent a possible intermediate step between diet and drug therapy.

General Methods for Examples 5-8

Subjects 278 free-living subjects were screened from the Canadian-Maltese Diabetes Study between the age of 45 and 65 years. This population is known to have one of the highest rates of diabetes (Katona et al. (1983)). Thirty eight of them satisfied the initial inclusion criteria: impaired glucose tolerance (IGT) (World Health Organization Diabetes Mellitus: Report of the World Health Organization Study Group. Technical report No. 727:9-15, 1985); clinical absence of CHD; body-mass index of less than 30 $kg/m^2$; not taking medications for hyperglycemia, hyperlipidemia or hypertension; not smoking; nor consuming more than two alcoholic drinks per day. These is subjects were further screened for the presence of the full multiple metabolic syndrome (Trevisan et al. (1998)) (syndrome X). This included moderate hypertension (>135/85 and less than 145/95 mm Hg), dyslipidemia (low-HDL [levels below 0.9 mmol/L for men and 1.2 mmol/L for women], and elevated triglycerides [greater than 2.3 mmol/L and less than 4.5 mmol/L]). Based on power analysis from the previous study (Vuksan et al. (1999)) and Example 1, eleven subjects (5 men, 6 women) who qualified were recruited. In addition to meeting the above criteria, their fasting (98±13 pmol/L) and 2-hour postprandial (439±68 pmol/L) plasma insulin levels was greater (p<0.05) than two standard deviation of the initial screening pool (71±8 and 316±47 pmol/L respectively). All eleven also had moderately high serum cholesterol (between 5.2 and 6.7 mmol/L) and were sedentary, with a mean (±SD) age of 55±4 years (range: 46-61 years); a BMI of 28±3 $kg/m^2$; a waist-hip ratio of 0.98±0.2 (waist: 96±12 cm) in men and 0.91±0.4 (waist: 87±19 cm) in women. They gave written informed consent to participate in the current study that was approved by the Human Ethic Committees of St. Michael's Hospital and the University of Toronto.

Study Design

The study employed a double-blind, placebo-controlled, cross-over design that was identical to that used in the previous study (Vuksan et al. (1999)) and Example 1. It began with an 8-week baseline period during which participants followed a National Cholesterol Education Program (NCEP) Step 2 (American Diabetes Association (ADA): Nutrition Recommendations and principles for people with diabetes mellitus. *Diabetes Care* 22:s42-s43, 1999)) ad libitum diet, documented by three non-consecutive days of food records every two weeks. This run-in phase was included to eliminate possible effects of dietary change on metabolic parameters. The experimental phase of the study followed. This consisted of two successive 3-week treatment periods, separated by a two-week washout interval over which a Step 2 diet was followed and documented by another three-day food record. During the first treatment period, subjects were randomly assigned to either the KJM+ (Step 2 metabolically controlled diet enriched with KJM+ fiber) or the control treatment (the same diet enriched with wheat bran [WB] fiber). For the second treatment period, the subjects were crossed-over. Blood collection, weight, blood pressure, and waist and hip measurements were done at the beginning and end of each 3-week treatment period. The study began with 5 subjects taking the KJM+ treatment and 6 the control.

Diet

Both treatments consisted of a three-day rotating Step 2 diet with three meals per day provided under metabolic conditions. All foods were pre-weighed, packaged and couriered to participants for consumption at home or at work. The mean macronutrient profile closely conformed to a Step 2 diet (of calories <30% from total fat, <7% from saturated fat, and <300 mg/day cholesterol) (American Diabetes Association (ADA): Nutrition Recommendations and principles for people with diabetes mellitus. Diabetes Care 22:s42-s43, 1999)). Energy intakes for weight maintenance were provided according to Lipid Research Clinics Tables with adjustment for physical activity (24). Total dietary fiber was administrated at 1.5 g/100 kcal, with a mean daily intake according to energy intake ranging from 24 g to a plateau of 40 g for those consuming 2800 kcal per day or more. The actual diet consumed is presented in Table 5.

The two treatments differed only in the type of fiber. On the KJM+ treatment, participants received KJM+ enriched test biscuits whereas on the WB-control treatment they received an equal quantity of wheat bran control biscuits. Subjects were instructed to eat an equal amount of biscuits together with an 8 oz beverage, 3 times daily as a snack, including once at bedtime. Both were provided by Dicofarm S.p.A, Roma, Italy. They had similar nutrient profiles and were indistinguishable in taste and appearance. KJM+ biscuits contained approximately 10% KJM flour of which 69% was the active high viscosity glucomannan, 15% other polysaccharides, and 16% excipients by weight (Vuksan et al. (1999)). The KJM flour mixture of the KJM+ biscuits comprised 69%+17% xanthan, 9% caragenan, and 8% guar. Because KJM flour comprised half (0.75 g/100 kcal) of the total fibre on the KJM+ treatment, approximately 0.5 g/100 kcal (8-13 g/day) was glucomannan. Wheat bran biscuits, in contrast, had a lower proportion of total dietary fiber than KJM+ biscuits. Approximately 1 g/day of wheat bran fibre derived from standardized American Association of Cereal Chemist hard red wheat bran was, therefore, added to the WB-control diet to compensate for these fiber differences. Subjects were instructed to sprinkle the additional fiber on cereal, yogurt, and/or other compatible foods to improve palatability.

Any foods from the metabolic diet together with study biscuits not consumed during the study were returned to the clinic for weighing to measure compliance. Dietary changes found to occur during the first three-week treatment period were duplicated in the diets for the second treatment period for each participant.

Laboratory Methods

Laboratory methods were identical to those used in (Vuksan et al. (1999)). In brief, blood samples were separated immediately and stored as serum in four aliquots at $-70°$ C. after collection. They were thawed at the end of the study for analysis of total cholesterol, HDL, and triglycerides measured enzymatically. LDL content was estimated by the formula of Friedewald et al. Apolipoprotein (Apo) A1 and B were determined by rocket immunoelectrophoresis. Fasting blood glucose was analyzed by a hexokinase method using a Cobas Mira Autoanalyzer (Roche Diagnostic, Mississauga, Canada). Serum fructosamine was analyzed in triplicate using Cobas Fara II and plasma insulin in duplicate by radioimmunoassay with reagent from ICN Biomedicals, Inc. (Horsham, Pa.). C-peptide was determined by radioimmunoassay.

Statistical Analyses

Results are expressed as mean±SEM, except for age, anthropometric measurements and nutrient intake (mean±SD). Data were analyzed by the Statistical Analysis System (SAS Institute, Cary, N.C.). Differences between the diets were assessed by two-tailed Student's t-test for paired data (univariate procedure). This same statistic also assessed differences in serum lipids, apolipoproteins, glycemia, blood pressure and body weight between the beginning (week-0) and end (week-3) of each treatment (WB-control and KJM+). Analysis of covariance (ANCOVA) with the facility of General Linear Model (GLM) procedure was used to test for differences in these same parameters between the two treatments. Control of individual variation from the repeat measures aspect of the design was addressed by incorporating the random subject effect as well as the starting measurement. Diet, sex, and phase effects were also incorporated in this model. Adjustment for multiple comparisons was made by the Bonferroni-Hochberg procedure (Hochberg (1988)). P-values for each endpoint were ordered sequentially and contrasted with the corresponding adjusted comparison-wise critical alpha ($\alpha$) levels. The null hypotheses were rejected only if p-values were less than their corresponding $\alpha$-values.

Example 5

All participants followed the experimental protocol with little difficulty. Returned food from metabolic diets indicated that subjects consumed an average of 96% and 95% of diet calories prescribed on the KJM+ and WB– control treatments respectively. Returned biscuits indicated they consumed 81% (97 g/day) of KJM+ and 86% (103 g/day) of WB-control biscuits. Consumption patterns translated into an insignificant decrease in body weight during both treatment periods with no difference between treatments (Table 6). The only side effect experienced was a transient complaint of flatulence and soft stools reported by 3 and 2 of the participants during the KJM+ and the WB-control treatments respectively, but none chose to discontinue the study.

Example 6

Blood lipids improved during KJM+treatment compared to WB-control (Table 6). Total and LDL cholesterol fell significantly by 19±9.7% (P<0.0001) and 29±3.4% (P<0.0001) during KJM+ treatment compared to 6.3±3.4% (P=0.088) and 6.6±5.0% (P=0.231) on control. The between-treatment differences were 12.4±3.1% (P<0.005) and 22±3.9% (P<0.003) respectively. The combined fall in total cholesterol from 6.9±0.3 to 5.0±0.2 mmol/L and LDL from 3.9±0.2 to 2.8±0.2 mmol/L on KJM+ treatment indicated reclassification of is the lipid status of the group (8 of 11 subjects) from elevated to normal cholesterolemia (National Cholesterol Education Program: Second report of the expert panel on detection, evaluation, and treatment of high blood cholesterol in adults(adult treatment panel II). *Circulation* 89:1333-1445, 1994)). Similar results were observed for Apo B. During KJM+ treatment Apo B fell significantly by 19±2.8% (P<0.0004) compared to 4.5±4.5% (P=0.34) on control, for a significant difference of 15.1±4.3% (P<0.0004) between the treatments.

In contrast, such effects were not seen on Apo A-1, or triglycerides. During KJM+ and control treatments, HDL decreased significantly on both treatments (8.5±9.2%, P<0.04 on KJM+ diet and 9.6±9.2%, P<0.003 on WB-control, with an insignificant between-treatment change (P=0.98). Similarly, during both treatments, triglycerides increased insignificantly, with no significant difference between treatments.

Despite this lack of effect of KJM+ treatment on HDL, Apo A-1, or triglycerides, the decreases in total cholesterol and Apo B were sufficient to improve lipid ratios. During KJM+ treatment total/HDL, LDL/HDL and Apo B/A-1 ratios decreased by 11±3.0% (P<0.005), 22±3.7% (P<0.0002) and 13±3.0% (P<0.003) respectively. This compares to an insignificant increase of 4.1±4.1% in total/HDL ratio, 0.2±6.3% in LDL/HDL ratio and 0.7±3.6% in Apo B/A-1 on WB-control. The resultant between-treatment differences were 15.2±3.4% (P<0.003) for total/HDL cholesterol, 22.2±4.1% (P<0.002) for LDUHDL cholesterol, and 13.1±3.4% (P<0.0003) for Apo B/A-1.

Example 7

An improvement in glycemic control was observed on the KJM+ treatment compared to WB-control (Table 6). Serum fructosamine was reduced during the KJM+ treatment by 5.6±1.5% (P<0.003), compared to 0.39±1.3% (P=0.77) on control, with a between-treatment difference of 5.2±1.4% (P<0.002). No significant between-treatment differences were seen for insulin or glucose concentrations. On KJM+ however, fasting glycemia fell by 13±2.5% (P<0.0001) compared to 9.6±4.3% (P<0.05) on control.

Example 8

No change in systolic or diastolic blood pressure was observed on either treatment or between treatments (Table 6).

All above results remained unchanged after adjustment for multiple comparisons by the Bonferroni-Hochberg procedure.

Discussion of Examples 5-8

These Examples demonstrate that the addition of 0.5 g/100 kcal (8-13 g/day) of high viscosity glucomannan in biscuit form to a high-carbohydrate/low-saturated fat NCEP Step 2 diet improved metabolic control beyond diet alone in individuals with the insulin resistance-dyslipidemic syndrome. Significant reductions in hyperglycemia as measured by the short-term marker of glycemic control, fructosamine, were observed. Also observed were significant reductions in hyperlipidemia as measured by total, LDL, LDL/HDL and total/HDL cholesterol, apo B and apo B/A-1, relative to a matched WB-control treatment. These findings represent the first to demonstrate such improvements using soluble fiber in individuals with this particular cluster of risk factors that also includes the intermediate diabetic classification, IGT. [syndrome X]

Because of the strong implications of this syndrome, a more aggressive approach has been suggested to achieve similar reductions. Diabetes and heart disease share common precursors for the development of atheroslerosis that often co-occur. Long before diabetes becomes manifest, the clustering of metabolic abnormalities exerts a synergistic effect on the atherosclerotic process (Haffner et al. (1990)). Based on findings from Trevisea and colleagues, cardiovascular disease (CVD) risk appears to increase linearly with an increase in the number of these risk factors. It is recommended therefore that insulin resistant patients have their CHD risk factors managed as if they have established coronary heart disease (Haffner et al. (1998)).

Low-fat/high carbohydrate diets may still have promise as a therapeutic approach. Although there has been a shift away from their advocacy in favor of those rich in monounsaturated fat (American Diabetes Association (ADA): Nutrition Recommendations and principles for people with diabetes mellitus. *Diabetes Care* 22:s42-s43, 1999), these diets supplemented with fiber may have similar metabolic advantages. Guar gum, pectin, oat products, and psyllium added to high carbohydrate diets have been shown to improve total and LDL cholesterol significantly, with no improvement to triglycerides and slight or no adverse effects on HDL (Jenkins et al. (1978)). Both guar (Aro et al. (1981)) and KJM+ (Arvill et al. (1995); Vuksan et al. (1999)) supplementation have also been shown to improve other risk factors, including glycemia and blood pressure. This lead to support for the use of guar in the treatment of the multiple metabolic syndrome (Landin et al. (1992)). Evidence further suggests that supplementation with these soluble fibers may augment concurrent drug therapy. Improvements in these assorted risk factors following supplementation have been noticed beyond what was achieved by drugs alone in subjects receiving hypolipidemic (Aro et al. (1981); Vuksan et al. (1999); Tuomilehto et al. (1989)), hypoglycemic (Aro et al. (1981); Vuksan et al. (1999); Shima et al. (1983)), and hypotensive (Vuksan et al. (1999); Uuistupa et al. (1984)) medications.

The ability of soluble fiber to improve a high carbohydrate/low fat diet is supported by the findings of these Examples. Total and LDL cholesterol were decreased and glycemic control was improved significantly. Also, although HDL, Apo A-1, and triglycerides were unaffected, as has been noticed with other fibers, this was balanced by the significant improvements in the other lipid endpoints, leading to significant reductions in all three lipid ratios: Total/HDL, LDL/HDL, and Apo B/A-1. Similar improvements in these ratios have rarely been reported using dietary interventions (Tuomilehto et al. (1989); Shima et al. (1983)). Overall, the present findings indicate that a Step-2 diet supplemented with KJM+ may confer additional benefits over the Step-2 diet alone, benefits that may be comparable to strategies using monounsaturated fat.

KJM+ may be better suited than the other major soluble fibers in improving outcomes with high-carbohydrate/low-fat diets. Although metaanalyses use variance adjusted values that tend to underestimate effectiveness, KJM+ can be compared to other soluble fibers in terms of its lipid lowering ability per gram of fiber, using recent meta-analytical data (Brown et al. (1999)). Daily intake of glucommanan from KJM+ on this study produced an average net change in total and LDL cholesterol of −0.084 and −0.119 mmol/L per gram of fiber respectively. These reductions represent approximately triple the lipid lowering capacity of psyllium (−0.028 and −0.029 mmol/L respectively), oat products (−0.037 and −0.032 mmol/L respectively), and guar gum (−0.037 and −0.033 mmol/L respectively) (Brown et al. (1999)). In the case of pectin, they represent comparable total cholesterol lowering capacity (−0.070 mmol/L) and approximately twice the LDL lowering capacity (−0.055 mmol/L) (Brown et al. (1999)). The very high viscosity of KJM+ used in this present study may explain these differences. It has been shown to be approximately five times higher than that of guar gum (Ebihara et al. (1989)) and beta-glucan (Wood (1990)), and considerably more than that of pectin (Venter et al. (1987)).

Contributions made by its theological properties may offer insight into the proposed mechanism by which the KJM+ supplemented biscuits had their beneficial effects. While not wishing to be bound to any particular theory, possibilities for its lipid lowering action may include an inhibition of cholesterol absorption in the jejunum (Venter et al. (1987) and bile acid absorption in the ileum (Kiriyama et al. (1974)) mediated by viscosity or less postprandial stimulation of HMG CoA reductase (Jenkins et al. (1993)). Other options include the generation of short chain fatty acids, predominantly propionate, by colonic microflora that may decrease hepatic cholesterol synthesis (Venter et al. (1990)). The improvement in glycemic control may be attributable to an effect of the gel forming KJM+ on rate of digestion. It has been suggested that decreases in glucose and insulin levels after the consumption of water-soluble fibers are related to slower rates of food absorption in the small intestine associated with increased viscosity (Jenkins et al. (1978)). This mechanism may explain why a reduction in serum fructosamine, but did not concomitant reductions in fasting glycemia and insulinemia were observed: KJM+ may be exerting its effect mainly postprandially.

In conclusion, the results in these Examples support the role of KJM+ mix as a means for improving high-carbohydrate diets in the amelioration of the insulin resistance-dyslipidemic syndrome. Improved metabolic control resulted in the correction of several risk factors that characterize the syndrome and figure prominently in the etiology of atherosclerotic CHD.

Example 9

Effect of Various PolySaccharides on Blood Glucose

Ten healthy male (3) and female (6) volunteers (Age=37; BMI=26.3 kg/m$^2$) were randomly assigned to consume either wheat bran control, Psyllium fiber, xanthan, KJM alone (FMC Co.) or KJM mix (preparation: KJM 74%, xanthan 26%) on five separate occasions. Each of the treatments contained 5 grams of above-mentioned ingredients which was added to 75 g available carbohydrate (300 ml) derived from glucose drink Glucodex solution (Technolab, Quebec) drink. Capillary blood glucose was taken after 10-12 hrs fasting and 15, 30, 45, 60 and 90 minutes after start of the test meals. Blood glucose was analyzed using YSI 2300 instrument. Results are presented as area under the glucose curve (FIG. 1) and absolute and incremental blood glucose levels (FIG. 2) for individual time points. The results indicated that the area under the glucose curve for KJM mix (39) was significantly lowered (P<0.011) than control treatment (113; p<0.02), psyllium (100; p<0.032), xanthan (81; p<0.041) and KJM alone (80; p<0.027). Incremental and absolute glucose levels were significantly reduced on KJM mix treatment at time 30 (P<0.05) compared to all other treatment.

Figure 2:
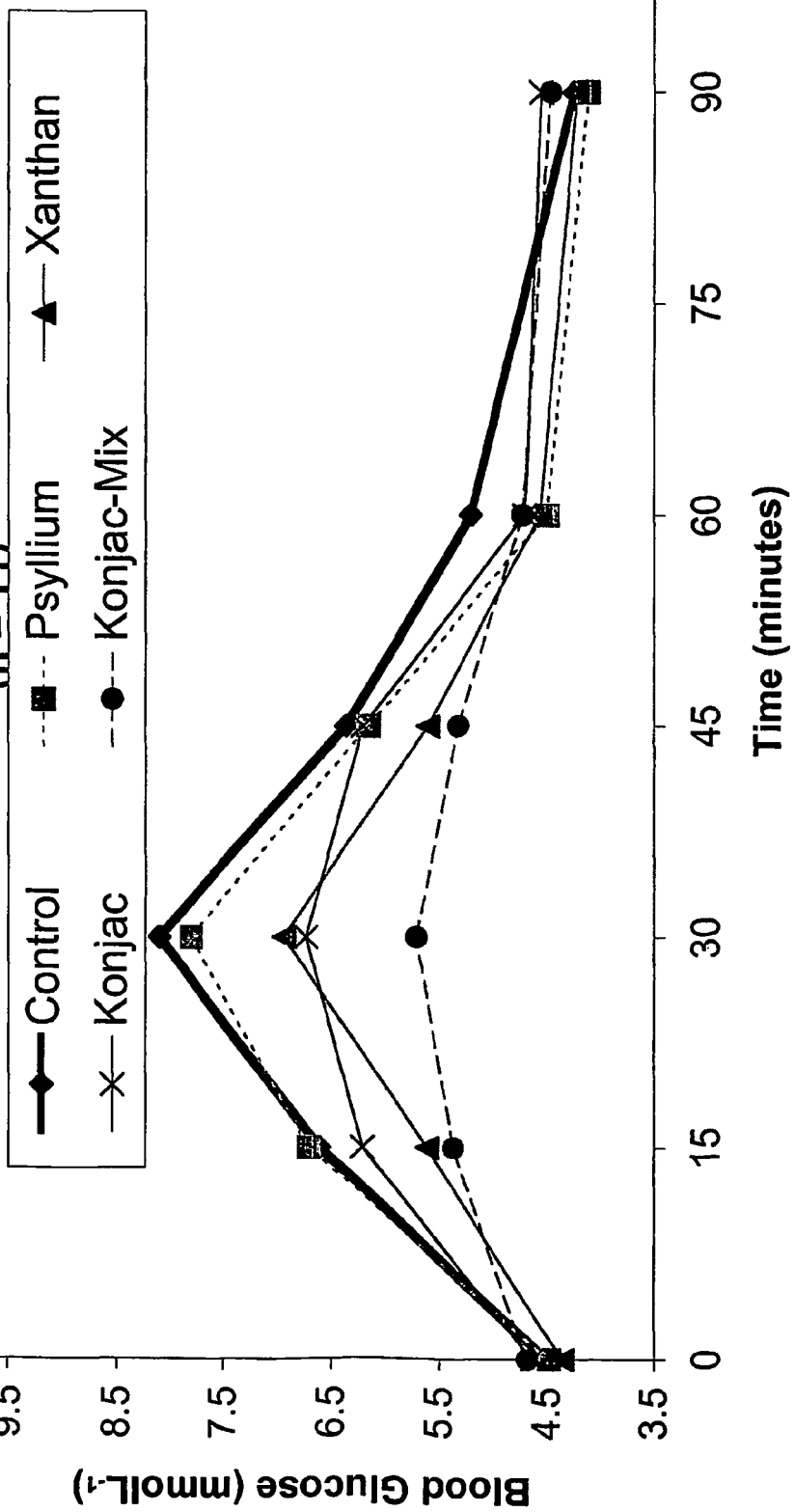
FIG. 2 is a graph illustrating the post-meal blood glucose response of individuals histogram illustrating the effect of various fibres including *Konjac-mannan* alone in comparison with a *Konjac-mannan* mixture of the present invention.

In summary, FIGS. 1 and 2 provide illustrations of the significant effects on blood glucose a *konjac* mannan mixture of the present invention has over the effects of individual saccharides and *konjac* mannan alone. The mixture of *konjac* mannan comprised *konjac* mannan and Xanthan although, other saccharides which can be use include, carragenan, acetan, guar, or xyloglucana.

Example 10

Figure 3:
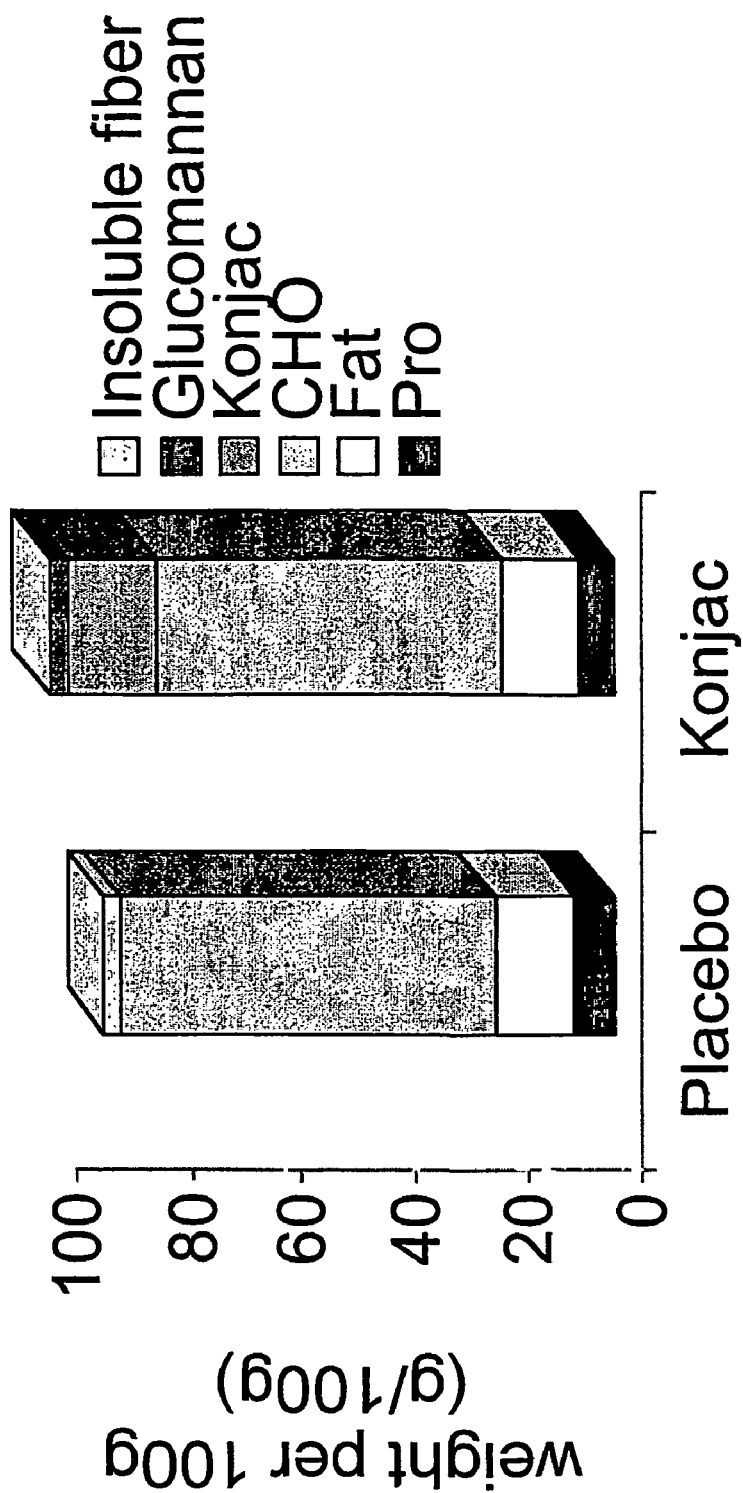
FIG. 3 is a bar graph illustrating the composition of the placebo versus *konjac* biscuits used in Example 10.
Figure 5B:
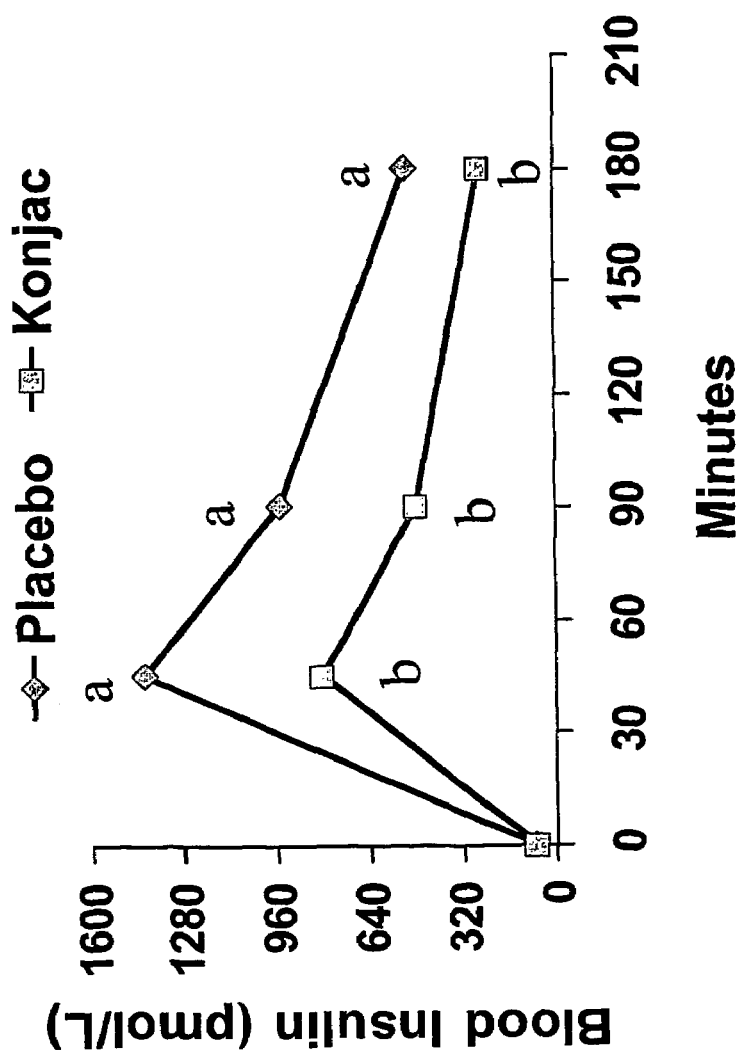

Chronic Feeding of *Konjac*-Mixture and Effect on Postprandial Glycemia in Insulin Resistance Atherosclerosis and diabetes have been characterized as postprandial phenomena. Recent epidemiological analyses demonstrated that diets with a low glycemic load reduce their incidence. To investigate the ability of KJM mix to reduce postprandial glycemia in the insulin resistance syndrome (syndrome X) that underlies these diseases, 12 participants were studied (age:55±4 y, BMI:28±3 kg/m$^2$) who satisfied the criteria for the syndrome (IGT, reduced-HDL, elevated triglycerides and mild-hypertension) following 21 days of KJM mix supplementation. In a crossover design, participants were assigned to take a metabolically controlled NCEP Step-2 diet either with 0.7 g/100 kcal of KJM mix enriched biscuits (as outlined in Examples 5-8), or matched wheat bran control biscuits over two 21 day treatment periods (see FIG. 3 for composition profiles). Venous blood samples were drawn at 0, 30, 45, 60, 90, 120, and 180 min after a standard breakfast (see Table 7), before (day-1) and after (day-3) chronic feeding of the KJM mix or wheat bran biscuits on each treatment period. Plasma glucose [FIG. 4A (day-1), FIG. 4B (day-3)] and insulin [FIG. 5A(day-1) and FIG. 5B (day-3)] concentration profiles were determined and whole body insulin sensitivity was calculated using both fasting and postprandial values, according to Matsuda and DeFronzo (Diabetes Care 1999; 22:1462-70). Area under the curves for glycemia (−23±5% versus 0.4±9.3%, P=0.000022)(FIG. 4C) and insulinemia (−40.5±4.5% versus −2.0±2.9%, p=0.000012) (FIG. 5C) were significantly reduced on the KJM mix treatment compared to wheat bran control treament. These decreases translated into a significant increase in postprandial insulin sensitivity on KJM compared to control (55.9±9.2% versus 9.7±4.5%, P=0.00056). Insulin sensitivity index (ISI) was calculated as follows:

Composite Whole Body ISI=10,000/(FPG×FPI)×(G×I)

Where 10,000 is the constant; Composite Whole Body ISI is hepatic & peripheral tissue insulin sensitivity, FPG is fasting plama glucose (mg/dL); FPI is fasting plasma insulin (µU/ml); G is mean glucose after glucose challenge; and I is mean insulin after glucose challenge.

From this it may be concluded that prolonged consumption of KJM improves glycemic control, as indicated by lower postprandial glycemia and insulinemia.

Example 11

Effect of Highly Refined *Konjac Mannan* and *Konjac Mannan* Mix on Postprandial Glycemia in Normal Individuals To determine the effect, if any, of viscosity of KJM fiber preparations on KJM activity, the efficacy of the KJM mix compared with highly refined commercially available KJM RS (Opta Co., U.S.) on lowering postprandial blood glucose levels was studied.

First viscosity measurements were taken of 2 KJM fibers, commercially available highly purified KJM RS produced by Opta C. (KJM 3) and the same KJM mixed with 23% of xanthan (KJM 1). To determine the difference in viscosity over time, 1.5 g of each KJM sample was mixed with 150 ml of water. Theological measurements using a Synchro-electric Viscometer (D.W. Brookfield Ltd., Cooksville, ON) (Shear 0.6/12, spindle E) were taken at 15, 30, 45, 60, 90, 120, 180 min and 24 h. Relative viscosity was compared between the samples. The two KJM fibres from Opta Co. (KJM 3) or the KJM mix (KJM 1) were compared in vivo testing. In vitro analysis indicated that viscosity of KJM 1(KJM mix) was significantly higher (42,000 cps) compared to commercially available most purified *konjac* RS fibre, KJM 3 (16,200 cps).

Figure 6A:
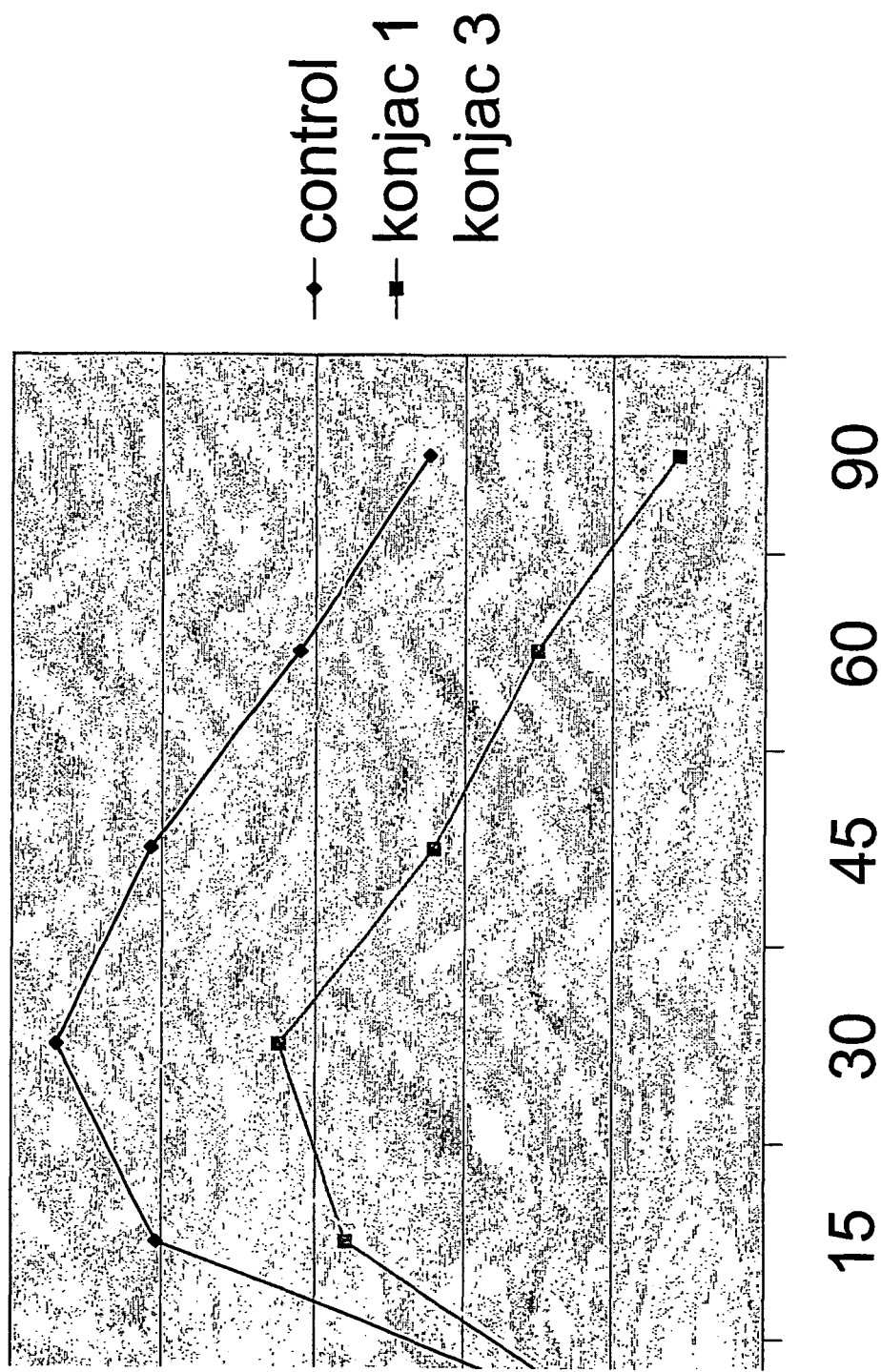
FIG. 6A is a linear graph illustrating absolute blood glucose levels.
Figure 6C:
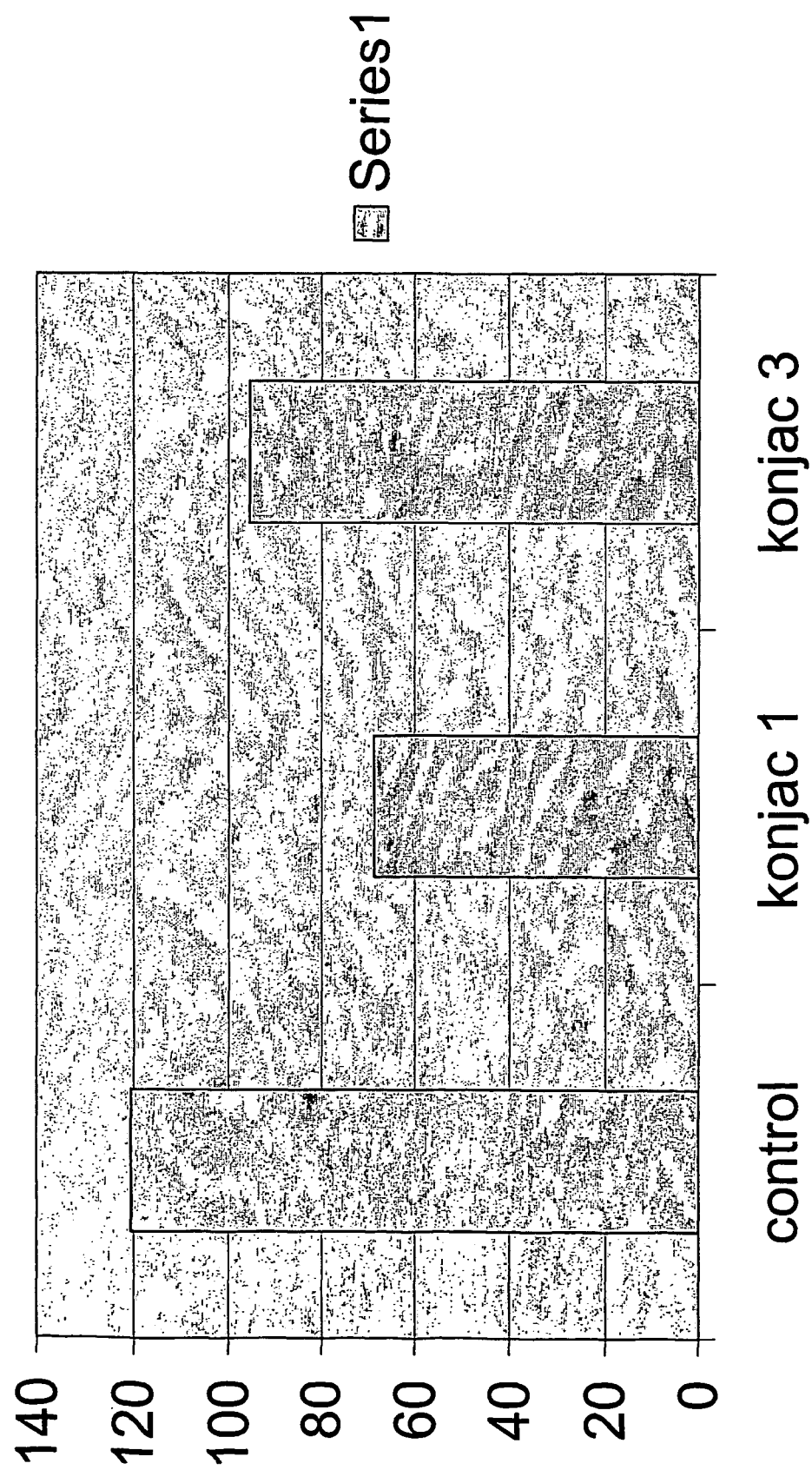
FIG. 6C is a bar graph illustration glucose area under the curve.

For the in vivo study seven healthy male (4) and female (3) volunteers (Age=43; BMI=24.7 kg/m$^2$) were randomly assigned to consume either wheat bran control, KJM RS (KJM 3) or KJM mixture treatment containing 23% of xanthan gum (KJM 1) on three separate occasions. Each of the treatments contained 3 grams of above-mentioned ingredients which was added to 50 g available carbohydrate (356 ml) derived from vanilla flavored Ensure™ drink (Ross Abbott Laboratories). Capillary blood glucose was taken fasting (i.e after a 10 to 12 hrs fast) and 15, 30, 45, 60 and 90 minutes after start of the test meals. Blood glucose was analyzed using YSI 2300 instrument. Results are presented as area under the glucose curve (FIG. 6C) and absolute and incremental blood glucose levels (FIGS. 6A and 6B) for individual time points. The results indicate that the area under the glucose curve for KJM 1 (68.4) was significantly lowered (by about 44%) (P<0.015) than control treatment (120.5), and KJM 3 (P<0.034) treatment (95.6) (lowered by about 21%). There were significant differences between the two KJM fibers on time. Incremental and absolute glucose levels were significantly reduced on KJM 1 treatment at time 60 (P<0.02) and 90 minutes (P<0.01) as compared to KJM 3 treatment. When compared to the control meal KJM 3 showed no significance difference at any time points, or for the area under the glucose curve. As such it can be concluded that KJM mixed with polysaccharides such as xanthan in proportion to act synergistically is more effective on postprandial glycemia than highly refined KJM alone. KJM in mixture with other polysaccharides will express its efficacy in glycemic control of healthy individuals.

Example 12

Effect of American Ginseng, *Konjac Mannaan* Mix and Combination Thereof on Postprandial Blood Pressure in Type 2 Diabetes The effect of the proprietary KJM MIX, AG, and their combination (AG&KJM MIX) on postprandial blood pressure regulation in type 2 diabetic individuals as compared with wheat bran control was studied. Seventeen healthy male (10) and female (7) volunteers (Age=64.7; BMI=29.4 kg/m$^2$) were randomly assigned to consume either wheat bran control, AG, KJM mixture treatment containing 27% of xanthan gum (KJM MIX), or combination of AG and KJM MIX, on four separate occasions. Each of the treatments contained 3 grams of above-mentioned ingredients which was added to 50 g available carbohydrate (356 ml) derived from vanilla flavored Ensure™ drink. Standardized lunch was served at 240 minutes time after start of breakfast. Blood pressure was taken −30 min, 0, 30, 60, 120, 240, 360, and 420 minutes after start of the test meals. Blood pressure was determined using conventional mercury sphyngomanometar device. Results are presented as systolic and diastolic blood pressure (See FIG. 7). When compared to the control treatment, systolic blood pressure (SBP) was significantly reduced after taking KJM MIX (at time30, 60, 120, and 360 minutes); KJM MIX and AG combined (at 30,60,120, and 240 minutes), whereas AG lowered SBP only at 30 min and 120 min after start of test breakfast. The diastolic blood pressure was not different between four treatments. Therefore, it can be concluded that KJM MIX and AG whether taken alone or in combination reduce SBP in type 2 diabetic individuals. Further, the effect of the combination of KJM and AG seems to be different than each individual component. This indicates that there is a different mechanism of action which might be beneficial and superior to wither of the two components alone.

Example 13

Effect of American Ginseng, *Konjac Mannaan* Mix and Combination Thereof on Postprandial Blood Pressure, Blood Glucose and Insulin in Type 2 Diabetes The effect of the proprietary KJM MIX, AG, and their combination (AG&KJM MIX) on postprandial blood pressure, blood glucose and insulin regulation in type 2 diabetic individuals as compared with wheat bran control was studied.

Seven volunteers with type 2 diabetes were recruited; duration of diabetes 8.4±4.9 yr, HbA1c 6.9±1%, 86.4±15.9 kg. The study utilized a crossover, double blind design. Four sets of breakfasts and lunches were administered in random order. Lunch was a standard meal, only the breakfast meal contained either wheat bran (control) or KJM mix with or without AG. The test days were randomized for each subject and were scheduled at least one week apart. The total test day spanned 7 hours. Blood samples were taken using an indwelling catheter at −30,0,5,10, 15,30,45,60,90,120,150, 180, 240 (lunch), 270, 300, 330, 360, 390 and 420 min. Samples will be analyzed for glucose and insulin.

Clinical blood pressure was measured using conventional mercury sphygmomanometer according to Joint National Council (JNC) VI criteria at −30, 0, 30, 60, 120, 240, 360, 420 min. Subjects were asked to record their satiety levels throughout the day using a bipolar scale ranging from −3 (extremely hungry), 0 (neutral), to +3 (uncomfortably full). The palatability of the meals was also recorded on a scale from 1 to 10, where 1 was "dislike extremely", 5 "neutral" and 10 "delicious". At each visit weight was measured using a beam scale and total body fat was measured with the Futrex 5000, using infrared technology. Additional samples were taken at the beginning and end of the study and measured for hemoglobin levels. This measurement was suggested by the Ethical Board of St Michael's Hospital as there was a concern regarding possible anemia.

The results indicated that weight and total body fat did not significantly differ for each intervention. Hemoglobin decreased significantly by 12.2 g/L. There were no differences between meals in palatability of either breakfast or lunch. The blood pressure results look promising.

Figure 9A:
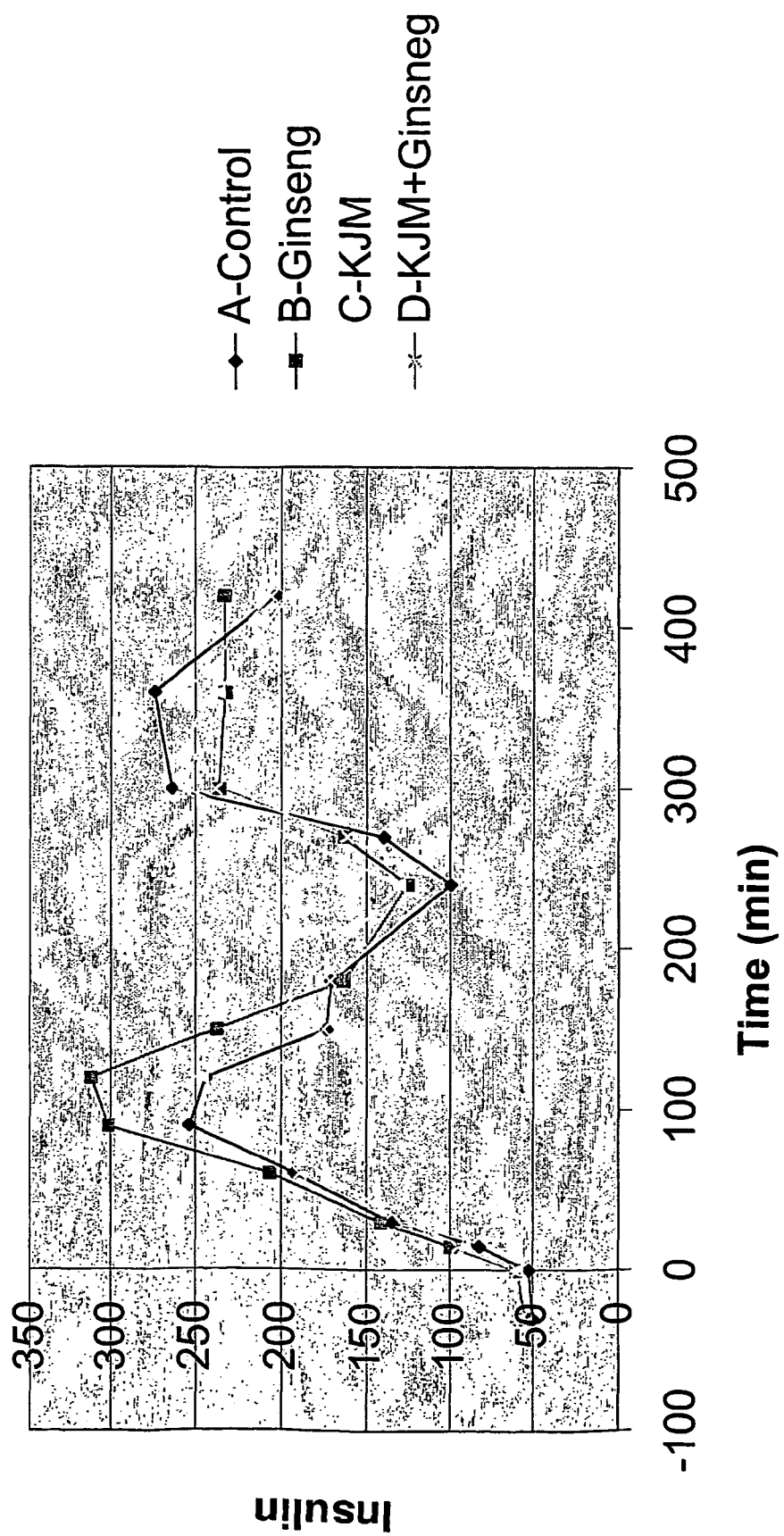
FIG. 9 is a linear graph illustrating insulin levels versus time using various treatment regimes: placebo, ginseng, *konjac* mannan mix, and *konjac* mannan mix and ginseng.

Postprandial blood glucose was significantly lower in all 3 interventions (KJM mix, AG, and its combination) compared to control wheat bran. The lowest results are found to be with combination of KJM mix and AG, indicating an additive effect of mixing the two compounds (FIGS. 8A and 8b). Insulin results indicated significantly higher insulin secretion, but lower on KJM mix and even lower when 2 compounds were combined. (FIG. 9)

Overall, the effect of KJM, and AG in the present study confirmed that they both beneficially affect postprandial glycemia. Postprandial blood glucose was lowered by two mechanisms that are different but complementary; ginseng increase insulin secretion and KJM mix reduces insulin levels (increases insulin sensitivity). The effect of the combination of KJM and AG seems to be different than each individual component. This indicates that there is a different mechanism of action which might be beneficial and superior to wither of the two components alone. The fact that blood glucose was lowest on KJM mix and AG combination with lowest insulin secreted, indicate that this combination provides the most effective and economic intervention of all three. Saving insulin (insulin economy) to achieve lowest blood glucose results would be extremely beneficial in a diabetes therapy.

Example 14

The Effect of Protopanaxadiol/Protopanaxatriol Ratios of Ginseng on Glucose Levels There are a wide variety of ginsengs and not all, even ones within the same species will necessarily have the same effect. As such the composition profiles of various ginsengs and their effect on blood glucose and insulin was studied.

The effect of ginsengs with different diols/triaols ratios was investigated. In series of successful clinical studies American ginseng was used, with composition of protopanaxadiols ($Rb_1$, $Rb_2$, Rc, and Rd) (diols) relative to protopanaxatriols ($Rg_1$, Re, Rf) (triols), that had a ratio of above approximately 1.5 (i.e. Chinese ginseng with 1.91 ratio and American with 1.51 and 2.44 ratio). As such ginseng with a specific ginsenoside profile significantly decreases glucose. Ginseng profiles with weight ratios lower then 1.5 were also studied.

Figure 10:
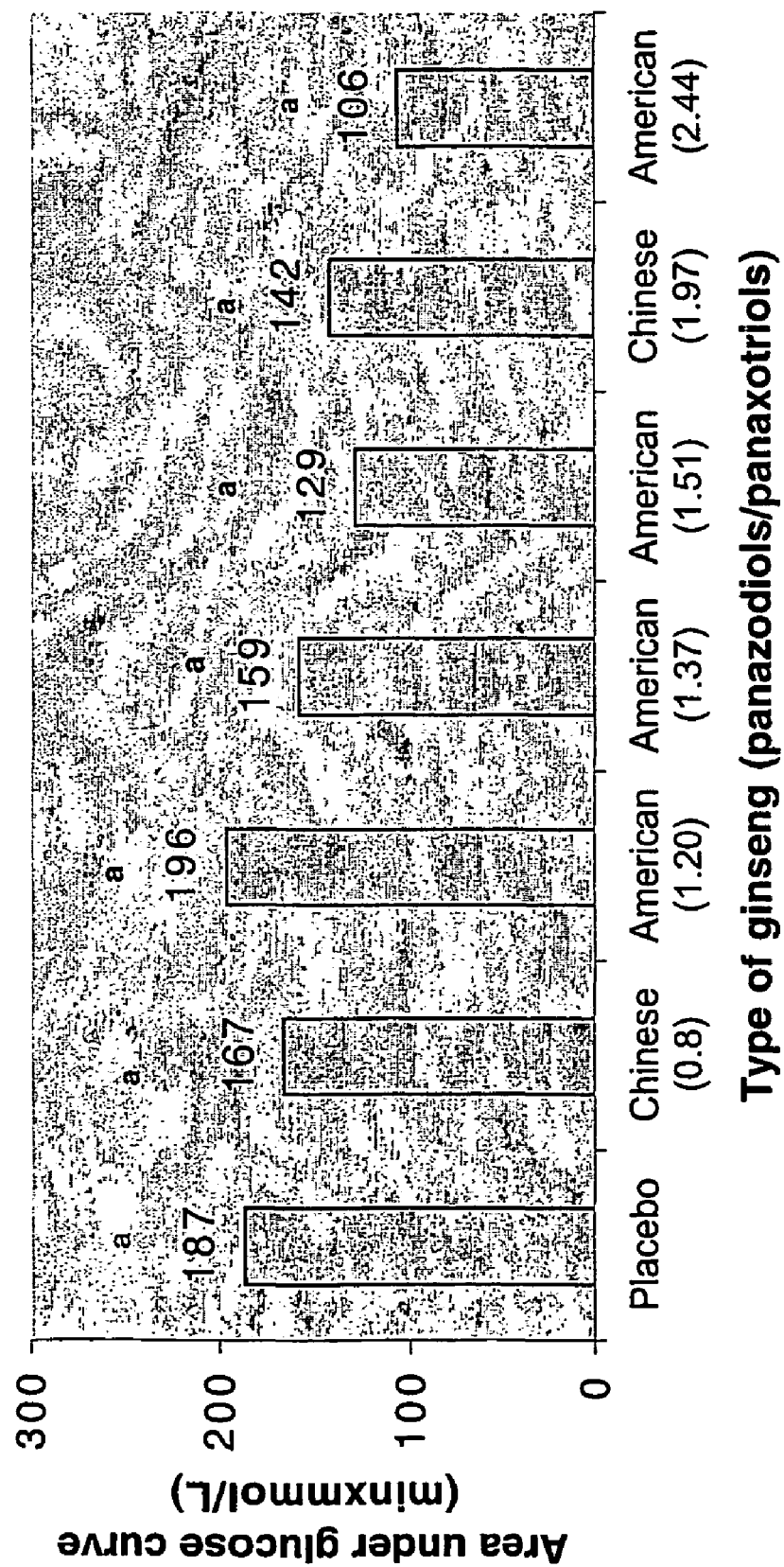
FIG. 10 is a bar graph illustrating the effect of various ginseng preparations with various diol/triol ratios on postpranial blood glucose levels.

In the studies, ginseng was given with a 75 g oral glucose tolerance test (OGTT) and compared the results to a similar study done previously with ginseng with higher ratios (FIG. 10). Normal subjects were studied with 3 different ginsengs; in a first study 12 (gender: 6m: 6f, age: 31±3 years, BMI: 28±2 $kg/m^2$) with Chinese ginseng with diaols/triols ratio of 0.8; in the second and third studies, 10 (gender: 4m: 6f, age: 41±6 years, BMI: 26.1±0.4 $kg/m^2$) with AG with diaols/triols ratio of 1.2 and 1.37, respectively. A single-blind, crossover design was used in which all subjects received control or 6 g, 40 min before a 75 g-OGTT. Control in the present study consisted of identical capsules containing cornstarch, whereas in the previous study it was the 75 g-OGTT done alone. Both protocols followed the Canadian Diabetes Association guidelines for the OGTT, with venous blood samples drawn at −40, 0, 15, 30, 45, 60, 90, and 120 min. Repeated measures analysis of variance demonstrated that there was no significant effect of the AG containing diols/triols ginsenosides with ratios lower then 1.5. on incremental change or area under the curve (AUC) for glycemia or insulinemia. That was in contrast with results where ginseng with ratios above approximately 1.5 had beneficial effects. One of the explanation for this discrepancy is that the level of total or specific active ginsenosides, possibly in dials fraction rather then trials fraction of ginseng. These data suggest that the ginsenoside profile of ginseng, particularly ratio between protopanaxadials to protopanaxatriols of above 1.5, so this play a role in its effects.

That part of ginseng's profile that gives improvement in human metabolism seems to be related to ginseng composition, mainly to ratios between main ginsneosides groups. The ginsenoside content of the 6 different ginseng grinded root and extracts used in the series of clinical studies was studied and found that reduction of blood glucose, lipids, and blood pressure; and also increase in insulin secretion, and nitric oxide, and reduction in oxidative stress had a high proportion of protopanaxadiols ($Rb_1$, $Rb_2$, Rc, and Rd) relative to protopanaxatriols ($Rg_1$, Re, Rf). The present study indicates that an optimal level of this ratio of ginseng to be effective should be higher then approximately 1.5 (FIG. 10).

In FIG. 10, each bar represents ginseng with different diols/triols ratio. Once a ratio is reached of approximately 1.5 or higher the postprandial blood glucose is significantly reduced (letter b vs. a on graph). The first bar (area=167) is Chinese ginseng root with ratio 0.8. The second bar (area=196) is American ginseng extract (75% water:alcohol 25%) with ratio 1.2. The third bar (area=159) is American root ginseng with ratio 1.37.Fourth bar (area=159) is American root ginseng with ratio 1.37. The fifth bar represents (area=129) is Chinese ginseng extract (59% water: 41% alcohol) and ratio of 1.91 and this reduced blood glucose significantly. The sixth bar represents (area=142) American root ginseng with ratio 1.51 and this also reduced blood glucose significantly. The seventh bar represents (area=109) is American ginseng root with ratio 2.44 and this reduce blood glucose significantly.

A further pilot study in healthy volunteers was conducted to explore the effect of the whole root ginseng versus an alcohol:water=55:45 extract, both with dials to trial ratio>1.5 with or without the addition of KJM mix. Results showed that both ginseng types and the KJM lowered the incremental glucose area and combining the ginseng with the KJM mix had an additional effect (results not shown).

Example 15

The Effect of American Ginseng on Insulin and Nitric Oxide

Figure 11:
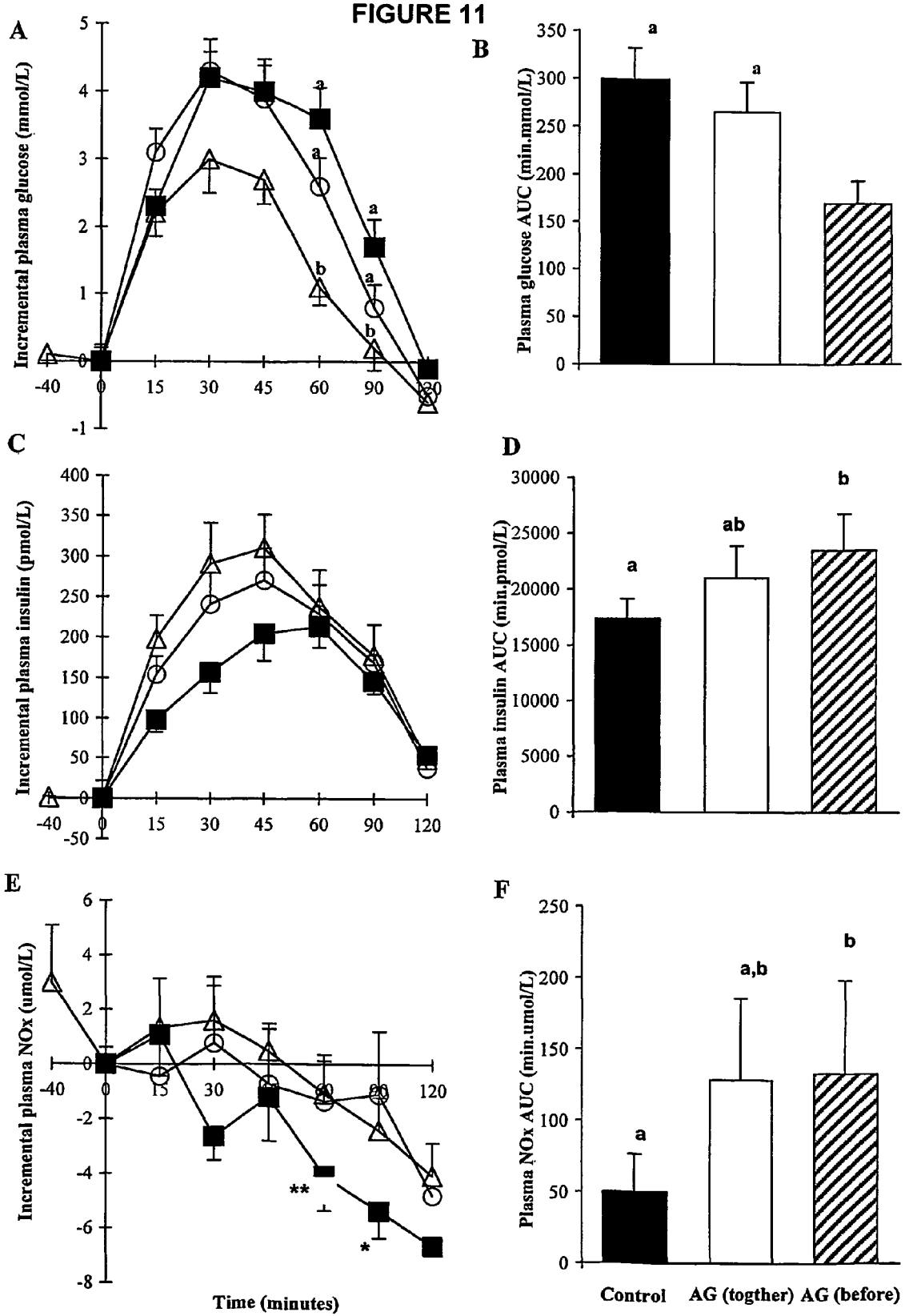
FIG. 11 illustrates a comparison of incremental change (linear graphs 11A, C, and E) and area under the curve (AUC) (FIGS. 11B, D, and F) in plasma glucose (FIGS. 11A and B), insulin (FIGS. 11C and D) and nitric oxide (Nox) (FIGS. 11E and F).

Other metabolic benefits such as increase in insulin secretion and nitric oxide generation (FIG. 11) are demonstrated with ginseng with ratio of above 1.5. In this study ginseng had ratios of diols/triols of 2.44. Ginseng was administrated to 8 (gender: 3m: 5f, age: 34±3 years, BMI: 24.6±0.8 kg $m^2$) healthy individuals. Data presenting reduction of postprandial blood glucose, and increase in plasma insulin and nitric oxide generation, relative to control. Data are presented in FIG. 11.

Comparison of incremental change and area under the curve (AUC) in plasma glucose, (FIG. 11A, 11B), insulin (FIGS. 11C and 11D) and nitric oxide (NOx) (FIGS. 11E and 11F) following ginseng (diols/trials ratio=2.44)) taken 40 min before (r) or together (O) with a 75 g oral glucose tolerance test (75 g-OGTT) or a 75 g-OGTT done alone previously (g) in 8 non-diabetic subjects. Glucose and insulin were measured by glucose oxidase method (67) and double antibody radioimmunoassay method respectively (68). Plasma NOx was measured as total nitrite ($NO_2^-$)+ nitrate ($NO_3^-$) concentrations by the chemiluminescence method (69,70) using a Sievers 280 NO Analyzer (Boulder Colo., USA). Points or bars with different letters are significantly different (repeated measures ANOVA adjusted for multiple pairwise comparisons with the Newman Keuls procedure, $P<0.05$). Data are mean±SEM.

Example 16

Effect of Ginseng on Postprandial Glycemia

The present inventor conducted four studies to determine the effect of American ginseng in humans were conducted (Table 8).

In the first of these studies, the glycemic responses in 10 normal and 9 type 2 diabetic subjects was studied after the administration of 3 g American ginseng or placebo given 40 minutes before (−40 minutes) or together with a 25 g oral glucose challenge. It was observed that selected blood glucose concentrations and the area under the curve were reduced significantly when ginseng was administered either before or together with the challenge compared to placebo in the diabetic subjects and only when given before in the normal subjects (Vuksan, *Arch.Intern. Med* 2000; 160:1009-13.

Similar reductions in postprandial glycemia both in non-diabetic and diabetic subjects were observed, in three subsequent acute dosing and timing response studies that followed (Table 8). The first of these two studies showed that 3, 6, or 9 g of American ginseng compared to placebo significantly reduced the postprandial glycemic response to a 25 g oral glucose challenge when administered 0 (together with), 40, 80, or 120 minutes before a glucose challenge in 10 diabetic subjects (Vuksan, *Doabetes Care* 2000; 23:1221-6) and when administered 40, 80, or 120 minutes before the challenge in 10 nondiabetic subjects (Vuksan, *J Am Coll Nutr* 2000: 18:738-744). There were no differences observed in either study between the doses or the times of administration in their glycemic lowering effect. These data suggested that ginseng is equally effective at doses above 3 g and when administered at any time together or before the challenge in diabetic subjects, but only when administered 40 minutes or more before the challenge in nondiabetic subjects. The third study showed that 1, 2, or 3 g of American ginseng compared to placebo reduced significantly the postprandial glycemic response to a 25 g oral glucose challenge when administered 40 minutes but not 20, 10, or 0 minutes before a glucose challenge in 12 nondiabetic subjects (Vuksan *Am. J Clin Nutr*, ). Again there were no differences detected between the doses studied. The suggestion was that ginseng is equally effective at doses above 1 g, but needs to be administered a minimum of 40 min before the challenge in nondiabetic subjects.

Having illustrated and described the principles of the invention in a preferred embodiment, it should be appreciated to those skilled in the art that the invention can be modified in arrangement and detail without departure from such principles. We claim all modifications coming within the scope of the following claims.

All publications, patents and patent applications referred to herein are incorporated by reference in their entirety to the same extent as if each individual publication, patent or patent application was specifically and individually indicated to be incorporated by reference in its entirety.

TABLE 1

Baseline Characteristics of the Study Subjects According to Sex*

| CHARACTERISTICS | MEN (N = 5) | WOMEN (N = 6) |
|---|---|---|
| Age - yr | 62 ± 8 | 59 ± 7 |
| Body weight - % desirable† | 133 ± 33 | 143 ± 22 |
| Android obesity - prevalence‡ | 5 | 4 |

TABLE 1-continued

Baseline Characteristics of the Study Subjects According to Sex*

| CHARACTERISTICS | MEN (N = 5) | WOMEN (N = 6) |
|---|---|---|
| Baseline values: | | |
| Serum total cholesterol - mmol/L | 6.2 ± 0.4 | 5.9 ± 0.5 |
| Glycosylated hemoglobin - % | 7.4 ± 2.1 | 8.3 ± 3 |
| Systolic/Diastolic pressure - mm Hg: | 139/78 | 136/82 |
| Known duration of: | | |
| Diabetes - yr (self-reported) | 11.5 ± 9 | 18.1 ± 6 |
| Hypertension - yr | 7.1 ± 3 | 6.0 ± 2 |
| Hyperlipidemia - yr | 6.3 ± 3 | 5.6 ± 2 |
| Drug/insulin treatment - prevalence: | | |
| Insulin | 1 | 3 |
| Sulfonylurea and/or Metformine | 5 | 6 |
| Diuretics | 2 | 4 |
| Other hypothensive | 4 | 3 |
| Lipid lowering medications§ | 5 | 6 |

*Except for drug treatment, blood pressure, and android obesity values are expressed as mean ± SD. To convert values for cholesterol to mg/dl multiply by 38.67.
†Values were assessed from Metropolitan Life Insurance tables, 1983.
‡Android obesity is indicated by a wait-to-hip ratio grater than 0.9 for men, and 0.8 for women
§Bile acid sequestrant, nicotinic acid and/or coenzyme A reductase inhibitor

TABLE 2

Average Intake of Energy and Nutrients in Eleven Subjects Before and During Study Periods.*

| Parameters | Baseline† | Konjac-mannan | Wheat Bran | P‡ |
|---|---|---|---|---|
| Total energy, kJ/d | 7671 ± 1760 | 8907 ± 2250 | 9134 ± 1006 | .23 |
| Total fat, % of energy | 24.8 ± 6.2 | 23.4 ± 2.1 | 23.9 ± 1.6 | .6 |
| Saturated fat, % of energy | 8.2 ± 2.4 | 4.1 ± .4 | 3.9 ± .2 | .73 |
| Monounsaturated fat, % of energy | 7.3 ± 1.3 | 12.4 ± 1.9 | 12.6 ± 1.4 | .35 |
| Polyunsaturated fat, % of energy | 9.1 ± 2.1 | 7.1 ± .2 | 7.6 ± .3 | .24 |
| Cholesterol, mg/4184 kJ | 87 ± 17 | 44 ± 18 | 36 ± 11 | .12 |
| Total protein, % of energy | 18.7 ± 4.2 | 15.5 ± 1.7 | 14.9 ± 2.1 | .86 |
| Available carbohydrate, % of energy | 56.5 ± 14.3 | 60.5 ± 8.6 | 61.2 ± 6.5 | .4 |
| Sugar, % of energy | 13.2 ± 17.2 | 11.2 ± .6 | 10.4 ± .3 | .17 |
| Total fiber, g/d | 27.4 ± 14.2 | 39.3 ± 11.4 | 40.1 ± 12.5 | .9 |
| Water soluble, g/d | 8.1 ± 2.7 | 23.1 ± 4.1 | 8.3 ± 2.4 | <.001 |
| Water insoluble, g/d | 17.8 ± 4.2 | 16.7 ± 3.6 | 29.8 ± 4.8 | <.001 |
| Sodium, mg | 4540 ± 1350 | 2820 ± 348 | 2708 ± 420 | .878 |
| Potassium, mg | 1430 ± 850 | 3960 ± 450 | 4240 ± 664 | .659 |
| Calcium, mg | 630 ± 442 | 1150 ± 185 | 1370 ± 246 | .552 |

*Values are mean ± SD. Konjac-mannan and wheat bran diets are based on actual intake. To convert kJ to kcal multiply by 2.39.
†Based on the mean of four non-consecutive 3-day food records.
‡Differences between the konjac-mannan and wheat bran study periods-were calculated by students paired t-test.

TABLE 3

Composition (g/100 g) of Konjac-mannan (KJM) and Wheat Bran biscuits, at the moisture content of 2.8 g/100 g.

| Biscuits Type | Protein | Fat | Available Carbohydrate* | KJM flour | Ash | Dietary Fiber$^H$ | Total Dietary Fiber — Glucomannan from KJM flour‡ | Energy§ (kJ/100 g) |
|---|---|---|---|---|---|---|---|---|
| Wheat Bran | 6.8 | 14.4 | 66.5 | — | 1.4 | 2.8 | — | 1011 |
| Konjac-mannan | 6.2 | 13.9 | 61.2 | 15.3 | 1.3 | 2.3 | 10.6 | 944 |

*Values are calculated by difference: 100 − (moisture + protein + fat + total dietary fiber + ash). Sucrose added is between 37-40% of total available carbohydrate.
$^H$Average values for dietary fiber in wheat bran and flour analyzed by method of Prosky et al. (1985).
‡Value represents 64% glucomannan polymer derived from KJM flour.
§Values for available carbohydrate expressed as monosaccharide. To convert kJ to kcal multiply by 2.39.

TABLE 4

Changes in Serum Lipids, Glycemia, Blood Pressure, Body Weight and 10-yrs. Coronary Heart Disease (CHD) Relative Risk during and between the Konjac-mannan and Control (Wheat Bran) Study Periods*.

| Risk factors | Konjac-mannan | | | Wheat Bran | | | Between - Treatments | |
|---|---|---|---|---|---|---|---|---|
| | Week-0 | Week-3 | Change, % | Week-0 | Week 3 | Change, % | Change, % | P |
| Cholesterol, mmol/L | | | | | | | | |
| Total | 6.10 ± 0.29 | 5.11 ± 0.28 | −16 ± 2.7§ | 5.81 ± 0.19 | 5.48 ± 0.19 | −4.9 ± 3.7 | −11 ± 4.3 | 0.0252 |
| LDL | 3.89 ± 0.25 | 3.04 ± 0.26 | −25 ± 3.9§ | 3.56 ± 0.18 | 3.29 ± 0.16 | −4.8 ± 5.9 | −19 ± 7 | 0.0331 |
| HDL | 1.07 ± 0.08 | 0.94 ± 0.06 | −11 ± 2.2‡ | 1.04 ± 0.10 | 0.95 ± 0.08 | −8.9 ± 2.4‡ | −2.2 ± 3 | 0.4924 |

TABLE 4-continued

Changes in Serum Lipids, Glycemia, Blood Pressure, Body Weight and 10-yrs. Coronary Heart Disease (CHD) Relative Risk during and between the Konjac-mannan and Control (Wheat Bran) Study Periods*.

| Risk factors | Konjac-mannan | | | Wheat Bran | | | Between - Treatments | |
|---|---|---|---|---|---|---|---|---|
| | Week-0 | Week-3 | Change, % | Week-0 | Week 3 | Change, % | Change, % | P |
| Triglyceride, mmol/L | 2.53 ± 0.23 | 2.88 ± 1.38 | 18.7 ± 12.8 | 2.69 ± 0.44 | 2.96 ± 0.37 | 25.1 ± 14.7 | −6.4 ± 14 | 0.6565 |
| Apolipoprotein, g/L | | | | | | | | |
| Apo A - 1 | 1.47 ± 0.07 | 1.37 ± 0.06 | −6 ± 3.1 | 1.48 ± 0.08 | 1.48 ± 0.10 | +0.7 ± 3.7 | −6.7 ± 4.3 | 0.1541 |
| Apo B | 1.50 ± 0.09 | 1.28 ± 0.08 | −14 ± 3.4‡ | 1.48 ± 0.08 | 1.40 ± 0.07 | −3.0 ± 5.0 | −11 ± 4 | 0.0253 |
| Lipid Ratios: | | | | | | | | |
| Total/HDL | 6.08 ± 0.48 | 5.69 ± 0.48 | −5.7 ± 2.4† | 6.06 ± 0.56 | 6.21 ± 0.53 | 4.7 ± 4.4 | −10 ± 4 | 0.0279 |
| Apo B/Apo A-1 | 1.05 ± 0.09 | 0.96 ± 0.08 | −8.6 ± 2.3‡ | 1.05 ± 0.10 | 0.99 ± 0.08 | −3.0 ± 4.5 | −3.2 ± 5 | 0.2353 |
| Glycemia: | | | | | | | | |
| Glucose, mmol/L | 9.63 ± 0.80 | 8.62 ± 0.95 | −11 ± 3‡ | 9.29 ± 0.74 | 8.99 ± 0.78 | −1.5 ± 6.1 | −9.7 ± 4 | 0.1413 |
| Fructosamine, mM | 3.43 ± 0.1 | 3.17 ± 0.2 | −6.1 ± 2.4† | 3.25 ± 0.2 | 3.25 ± 0.2 | −0.5 ± 1.4 | −5.7 ± 1.7 | 0.0069 |
| Insulin, pmol/L | 154 ± 38.6 | 150 ± 32.8 | 9.58 ± 9.7 | 142 ± 31 | 140 ± 31 | 2.1 ± 11 | −7.5 ± 12 | 0.559 |
| Blood pressure, mm Hg | | | | | | | | |
| Systolic | 139.5 ± 5.0 | 131.6 ± 4.9 | −5.5 ± 1.4‡ | 128.8 ± 4.0 | 130.4 ± 4.7 | 1.4 ± 2.7 | −6.9 ± 2.5 | 0.0211 |
| Diastolic | 79.1 ± 2.0 | 77.5 ± 1.8 | −1.6 ± 2.8 | 78.3 ± 1.6 | 78.4 ± 2.7 | 0.4 ± 3.6 | −2 ± 5 | 0.7056 |
| Body weight, kg | 85.6 ± 19 | 85.0 ± 19 | −0.6 ± 0.5 | 85.9 ± 19 | 85.3 ± 19 | −0.6 ± 0.4 | −0.1 ± 0.4 | 0.8991 |
| CHD Realtive Risk (10 yr) | 1.77 ± 0.2 | 1.50 ± 0.2 | −14 ± 2.7§ | 1.56 ± 0.2 | 1.63 ± 0.3 | 8.7 ± 7.3 | −22 ± 4.7 | 0.0107 |

*Except body weight (mean ± SD) values are expressed as mean ± SEM. Abbreviations are defined as LDL, low-density lipoprotein; HDL, high-density lipoprotein: Apo, apolipoprotein. To convert cholesterol, triglycerides, and glucose to mg/dl multiply by 38.67, 88.57, and 18, respectively.To convet insulin to µU/ml. multiply by 0.1394. All means are for n = 11 except for LDL where n = 9, since two subjects had triglycerides above 4 mmol/L preventing calculation by Friedewald equation. Within treatment differences were assessed by paired t-test |(†) P < .05; (‡) P < .01: (§) P < .001|,while between treatment differences by ANCOVA (PROC GLM). Lack of notation indicates no significant differences.
|(†&) P < .05; (‡$) P < .01; (§#) P < .001|.

TABLE 5

Average Intake of Energy and Nutrients Before and During Study Periods in Eleven Subjects

| Parameters | Baseline | KJM | WB |
|---|---|---|---|
| Total energy (kcal/d) | 2070 ± 700 | 2579 ± 628 | 2355 ± 420 |
| Total fat (% of energy) | 30.5 ± 4.3 | 29.3 ± 3.2 | 28.7 ± 2.4 |
| Saturated fat (% of energy) | 7.2 ± 4.7 | 6.7 ± 0.8 | 6.4 ± 0.7 |
| Monounsaturated fat (% of energy) | 10.3 ± 5.1 | 12.7 ± 2.1 | 12.2 ± 2.6 |
| Polyunsaturated fat (% of energy) | 13.0 ± 5.7 | 9.9 ± 1.8 | 10.1 ± 0.9 |
| Cholesterol (mg/d) | 328 ± 102 | 219 ± 48 | 236 ± 77 |
| Total protein (% of energy) | 14.6 ± 8.2 | 16.2 ± 2.7 | 15.6 ± 3.2 |
| Available carbohydrate (% of energy) | 54.9 ± 2.1 | 54.5 ± 9.4 | 55.7 ± 7.3 |
| Sugars (% of energy) | 13.3 ± 3.6 | 11.2 ± 0.9 | 9.2 ± 1.4 |
| Total fiber (g/d) | 24.2 ± 1.1 | 34.7 ± 8.4 | 33.4 ± 9.6 |
| Water soluble (g/d) | 6.9 ± 3.2 | 23.4 ± 1.7 | 9.9 ± 3.2* |
| Water insoluble (g/d) | 17.3 ± 7.3 | 11.2 ± 3.8 | 23.1 ± 2.6* |
| Sodium (mg) | 5810 ± 2384 | 3162 ± 648 | 3380 ± 647 |
| Potassium (mg) | 3882 ± 713 | 4530 ± 611 | 4840 ± 872 |
| Calcium (mg) | 1366 ± 193 | 1260 ± 238 | 1487 ± 446 |

TABLE 6

Changes in Serum Lipids, Glycemia, Blood Pressure, and Body Weight during and between the Konjac-mannan (KJM) and Wheat Bran Control (WB-Control) Study Periods in Eleven Subjects

| Risk factors | KJM | | | WB-Control | | | Between - Treatments | |
|---|---|---|---|---|---|---|---|---|
| | Week-0 | Week-3 | Change, % | Week-0 | Week-3 | Change, % | Change, % | P* |
| Cholesterol (mmol/L) | | | | | | | | |
| Total | 6.2 ± 0.3 | 5.0 ± 0.2 | −19 ± 2.69* | 6.0 ± 0.2 | 5.6 ± 0.2 | −6.3 ± 3.36 | −12.4 ± 3.1 | 0.0038* |
| LDL | 3.9 ± 0.2 | 2.8 ± 0.2 | −29 ± 3.37* | 3.8 ± 0.2 | 3.5 ± 0.2 | −6.6 ± 5.04 | −22.3 ± 3.9 | 0.0017* |
| HDL | 1.0 ± 0.1 | 0.9 ± 0.1 | −8.5 ± 2.19* | 1.0 ± 0.1 | 0.9 ± 0.1 | −9.6 ± 2.24* | 1.2 ± 2.2 | 0.9812 |
| Triglyceride (mmol/L) | 2.8 ± 0.2 | 3.0 ± 0.2 | 10.1 ± 9.92 | 2.9 ± 0.4 | 3.0 ± 0.3 | 12.1 ± 14 | −1.6 ± 10 | 0.7317 |
| Apolipoprotein (g/L) | | | | | | | | |
| Apo A - 1 | 1.4 ± 0.1 | 1.4 ± 0.1 | −6.5 ± 2.46* | 1.5 ± 0.1 | 1.4 ± 0.1 | −4.8 ± 3.38 | −1.8 ± 3.1 | 0.3622 |
| Apo B | 1.6 ± 0.1 | 1.3 ± 0.1 | −19 ± 2.78* | 1.6 ± 0.1 | 1.5 ± 0.1 | −4.5 ± 4.47 | −15.1 ± 4.3 | 0.0003* |
| Lipid Ratios: | | | | | | | | |
| Total/HDL | 6.5 ± 0.5 | 5.7 ± 0.4 | −11 ± 3.02* | 6.2 ± 0.4 | 6.4 ± 0.5 | 4.14 ± 4.16 | −15.2 ± 3.4 | 0.0023* |
| Apo B/Apo A-1 | 1.1 ± 0.1 | 1.0 ± 0.1 | −13 ± 3.02* | 1.1 ± 0.1 | 1.1 ± 0.1 | 0.72 ± 3.61 | −13.1 ± 3.4 | 0.0002* |
| LDL/HDL | 4.2 ± 0.4 | 3.2 ± 0.3 | −22 ± 3.72* | 3.9 ± 0.3 | 3.9 ± 0.4 | 0.22 ± 6.27 | −22.2 ± 4.1 | 0.0012* |
| Glycemic Control: | | | | | | | | |
| Glucose (mmol/L) | 6.8 ± 0.5 | 5.9 ± 0.3 | −13 ± 2.48* | 6.6 ± 0.3 | 5.9 ± 0.4 | −9.6 ± 4.27 | −3.8 ± 3.6 | 0.7653 |
| Fructosamine (mM) | 286 ± 13.6 | 269 ± 11.9 | −5.6 ± 1.46* | 279 ± 11.7 | 278 ± 12.6 | −0.39 ± 1.3 | −5.2 ± 1.4 | 0.0013* |
| Insulin (pmol/L) | 94.8 ± 16.6 | 91.1 ± 16.5 | 0.91 ± 8.88 | 99.2 ± 16.5 | 88.5 ± 11.4 | −3.0 ± 9.67 | 3.9 ± 8.9 | 0.9683 |
| Blood pressure (mm Hg) | | | | | | | | |
| Systolic | 139 ± 2.0 | 135 ± 3.6 | −2.9 ± 1.88 | 135 ± 2.6 | 138 ± 3.7 | 2.2 ± 2.5 | −5.1 ± 2.2 | 0.448 |
| Diastolic | 85.4 ± 1.8 | 84.8 ± 1.5 | −0.26 ± 2.55 | 85.5 ± 1.7 | 86.5 ± 1.5 | 1.33 ± 1.49 | −1.4 ± 2.1 | 0.2647 |
| Body weight (kg) | 80.7 ± 5.1 | 80.6 ± 5 | −0.17 ± 0.14 | 81 ± 5.3 | 80.6 ± 5.1 | 0.29 ± 0.35 | 0.1 ± 0.2 | 0.5303 |

TABLE 7

Test Breakfast Compositions

| Placebo Breakfast | Konjac Breakfast |
|---|---|
| 49 g W. Bran Cookies | 58 g Konjac Cookies |
| 52 g Branflakes | 69 g Branflakes |
| 250 ml 2% Milk | 250 ml 2% Milk |
| 8 g Butter | 8 g Butter |

| Macronutrient | Composition | |
|---|---|---|

TABLE 7-continued

Test Breakfast Compositions

| | | |
|---|---|---|
| Energy (Kcal) | 673 | 678 |
| Protein (%) | 10.3 | 11.2 |
| Total Fat (%) | 29.0 | 28.6 |
| Available Carbo (%) | 61.1 | 59.2 |
| Total Fiber (g) | 13.0 | 13.1 |
| Soluble Fiber (g) | 7.2 | 1.4 |

TABLE 8

| Study | Sample | Treatments | OGTT | AUC Reductions | P value |
|---|---|---|---|---|---|
| Study 1 | 10 NGT (Age: 34 ± 7 years, BMI: 25.6 ± 3 kg/m$^2$) | 3 g AG vs placebo @ 0 min<br>3 g AG vs placebo @ −40 min | 25 g | —<br>18% | P = NS<br>P < 0.05 |
| | 9 T2DM (Age: 62 ± 7 years, BMI: 29 ± 5 kg/m$^2$, HbA$_{1c}$: 7.6 ± 0.5%) | 3 g AG vs placebo @ 0 min<br>3 g AG vs placebo @ −40 min | 25 g | 19%<br>22% | P < 0.05<br>P < 0.05 |
| Study 2 | 10 NGT (Age: 41 ± 13 years, BMI: 24.8 ± 3.5 kg/m$^2$) | Dosing: 3, 6, or 9 g AG vs placebo<br>Timing: −40 min vs −120 or −80 min | 25 g | 26.6, 29.3, 38.5% for 3, 6, and 9 g | P < 0.05<br>P = NS<br>P = NS |

TABLE 8-continued

| Study | Sample | Treatments | OGTT | AUC Reductions | P value |
|---|---|---|---|---|---|
| Study 3 | 10 T2DM (Age: 63 ± 2 years; BMI: 27.7 ± 1.5 kg/m$^2$; HbA$_1$c: 7.3 ± 0.3%) | Dosing: 3, 6, or 9 g AG vs placebo Timing: −120, −80, −40 or 0 min | 25 g | 19.7, 15.3, 15.9 % for 3,6, and 9 g | P < 0.05 P = NS |
| Study 4 | 12NGT (Age: 42 ± 7 years, BMI: 24.1 ± 1.1 kg/m$^2$) | Dosing: 1, 2, or 3 g AG vs placebo Timing: −40 min vs −20, −10 or 0 min | 25 g | 14.4, 10.6, 9.1 % for 1,2, and 3 g 14.1, 15.0, 9.2 % for −40 min | P < 0.05 P < 0.05 |

AG, NGT, OGTT, T2DM, NS denote American ginseng, normal glucose tolerance, oral glucose tolerance test, type 2 diabetes mellitus, and nonsignificant respectively. P-values are for repeated measures analysis of variance (ANOVA) comparisons between absolute values. Values are mean ± SD.

DETAILED LEGENDS OF THE TABLES

Table 1

\* Except for drug treatment, blood pressure, and android obesity values are expressed as mean±SD.

† Values were assessed using Metropolitan Life Insurance tables, 1983.

‡ Android obesity is indicated by a wait-to-hip ratio grater than or equal to 0.9 for men, and 0.8 for women § Bile acid sequestrants and/or HMG-coenzyme A reductase inhibitors.

Table 2

\* Values are mean±SD. *Konjac-mannan* and wheat bran diets are based on actual intake.

† Based on the mean of four 3-day food records.

‡ Differences between *Konjac-mannan* and wheat bran study periods were calculated by students t-test for paired data.

Table 3

\* Values are calculated by difference: 100−(moisture+protein+fat+total dietary fiber+ash). Added sucrose was between 37-40% of total available carbohydrate.

† Average values for dietary fiber in wheat bran and flour analyzed by method of Prosky et al., 1985.

‡ Value represents 69% glucomannan polymer derived from KJM flour.

Table 4

\* Except for body weight (mean±SD), all values are expressed as mean±SEM.

† Between treatment differences assessed by ANCOVA (PROC GLM)

‡ Comparisonwise alpha (α) level was adjusted for multiple endpoint comparisons with the Bonferroni-Hochberg procedure for primary and secondary endpoints separately.

§ Significant after adjustment of alpha level by the Bonferroni-Hochberg procedure. Null-hypotheses were rejected only if the p-values were less than their corresponding α-value. P-values for during-treatment changes were assessed by paired t-test ∥ LDL values are for nine subjects, since two subjects had triglycerides above 4.5 mmol/L preventing calculation by Friedewald equation.

Table 5

Data are mean±SD. KJM+ and WB-control diets are based on actual intake. Baseline values are based on the mean of four 3-day food records. \*P<0.001 for differences between KJM+ and WB-control treatments (student's t-test for paired data)

Table 6

Data are expressed as mean±SEM, except for body weight which is mean±SD. Within-treatment differences (week-0 versus week-3) were assessed by paired Student's t-test and between-treatment differences by ANCOVA (GLM procedure). \*Significant after adjustment of alpha level by the Bonferroni-Hochberg procedure. Null-hypotheses were rejected only if the p-values were less than their corresponding α-value.

Table 7

Shows the Test Breakfast used in Example 10.

Table 8

Is a comparison of 4 studies. See Example 16.

FULL CITATION S FOR REFERENCES REFERRED TO IN THE SPECIFICATION

Alison K, Ryttig K R, Hylander B, Rossner S: A dietary fibre supplement in the treatment of mild hypertension. A randomized, double-blind, placebo controlled trial. *J Hypertens* 10:195-199, 1992

American Diabetes Association (ADA): Nutrition Recommendations and principles for people with diabetes mellitus. *Diabetes care* 22:S42-S43, 1999

Anderson J W, Tietyen-Clark J: Dietary fiber: hyperlipidemia, hypertension, and coronary heart disease. *Am J Gastroenterol* 81:907-919, 1986

Aro A, Uusitupa M, Voutilainen E, Hersio K, Korhonen T, Siitonen O: Improved diabetic control and hypocholesterolaemic effect induced by long-term dietary supplementation with guar gum in type 2 (insulin-independent) diabetes. Diabetologia 21:29-33,1981

Arvill A, Bodin L: Effect of short-term ingestion of *Konjac* glucomannan on serum cholesterol in healthy men. *Am J Clin Nutr* 61:585-589, 1995

Brown L, Rosner B, Willett W W, Sacks F M: Cholesterol-lowering effects of dietary fiber: a meta-analysis. *Am J Clin Nutr* 69:30-42, 1999

Burt V L, Cutler J A, Higgins M, Horan M J, LaBarthe D, Whelton P, Brown C, Rocella E J: Trends in the prevalence, awarness, tretment and control of hypertension in the adult U.S. population: data from the Health Examination Surveys, 1960-1991. *Hypertension* 26:60-69, 1995

DCCT Research Group: The effect of intensive treatment of diabetes on the development and progression of long-term complications in insulin-dependent diabetes mellitus. The diabetes control and complications trial. *New Engl J Med* 329:977-986, 1993

Doi K, Matsuura M, Kawara A, Baba S: Treatment of diabetes with glucomannan *Konjac* mannan. *Lancet* 1:987-988, 1979

Eastwood M A, Morris E R. Physical properties of dietary fiber that influence physiological function: a model for polymers along gastrointestinal tract. *Am J Clin Nutr* 55:436-442, 1992

Ebihara K, Masuhara R Kiriyama S: Major determinants Plasma glucose-flattening activity of a water-soluble dietary fiber: effects of *konjac-mannan* on gastric emptying and intraluminal glucose diffusion. *Nutr Reports Intl* 23:1145-1156, 1981

Ebihara K, Schneeman B O: Interaction of bile acids, phospholipids, cholesterol and triglycerides with dietary fibers in the small intestine of rats. *J Nutr* 119:1100-1106, 1989

Executive Summary of the Third Report of the National Cholesterol Education Program (NCEP) Expert Panel on Detection, Evaluation, and Treatment of High Blood Cholesterol in Adults. JAMA;285:2486-2497,2001

Friedewald W T, Levy R I, Fridrickson D S: Estimation of plasma low-density lipoproteins, cholesterol concentration without use of the preparative ultracentrifuge. *Clin Chem* 18:499-502, 1972.

Fruchart J C, Kora I, Cachera C, Clavey V, Duthilleul P, Moschetto Y: Simultaneous measurements of plasma apolipoproteins A-1 and B by electroimmunoassay. *Clin Chem* 28:59-62, 1982.

Goldsmith M G, Barrett-Connor E, Edelstein S L, Wingard D L, Cobin B T, Herrman W H: Dislipidemia and ischemic heart disease mortality among men and women with diabetes. *Circulation* 89:991-997,1994

Gu K, Cowie C C, Harris M I: Mortality in Adults With and Without Diabetes in a National Cohort of the U.S. Population, 1971-1993. *Diabetes Care* 21:1138-1145, 1998

Haffner S M, Stern M P, Hazuda H P, Rosenthal M, Knapp J A, Malina R M: Role of obesity and fat distribution in non-insulin-dependent diabetes mellitus in Mexican Americans and non-Hispanic whites. *Diabetes Care* 9:153-161, 1986.

Haffner S M, Stern M P, Hazuda H P, Mitchell B D, Patterson J K: Cardiovascular risk factors in confirmed prediabetic individuals. Does the clock for coronary heart disease start ticking before the onset of clinical diabetes? *JAMA* 263:2893-8, 1990

Haffner S M, Lehto S, Ronnemaa T, Pyorala K, Laakso M: Mortality from coronary heart disease in subjects with type 2 diabetes and in nondiabetic subjects with and without prior myocardial infarction. *N Engl J Med* 339: 229-34, 1998

Harris M I, Flegal C M, Cowie C C, Eberhardt M S, Goldstein D E, Little R R, Weidmeyer H-M, Byrd-Holt D D: Prevalence of diabetes, impaired fasting glucose, and impaired glucose tolerance in U.S. adults: The Third National Health and Nutrition Survey, 1988-1994. *Diabetes Care* 21(4):518-524, 1998

Helmrich S P, Ragland D R, Leung R W, Paffenbarger R S Jr.: Physical activity and reduced occurrence of non-insulin-dependent diabetes mellitus. *N Engl J Med* 325: 147-152, 1991

Himswarth H: Diabetes mellitus: a differentiation into insulin-sensitive and insulin-insensitive types. *Lancet i*: 127-130, 1936

Hochberg Y: A sharper Bonferroni procedure for multiple test significance. *Biometrika* 75:800-802, 1988

Hunninghake D B, Stein E A, Dujovne C A, Harris W S, Feldman E B, Miller V T, Tobert J A, Laskarzewski P M, Quiter E, Held J, Taylor A M, Hoffer S, Leonard S B, Brewer B K: The efficacy of intensive dietary therapy alone or combined with lovastatin in outpatient with hypercholesterolemia. *N Engl J Med* 328:1213-1219,1993

Jenkins D J, Wolever T M, Leeds A R, Gassull M A, Haisman P, Dilawari J, Goff D V, Metz G L, Alberti K G: Dietary fibres, fibre analogues, and glucose tolerance: importance of viscosity. Br Med J 1:1392-4, 1978

Jenkins D J A, Wolever T M S, Rao A V, Hegele R A, Mitchell S J, Ransom T P P, Boctor D L, Spadafora P J, Jenkins A L, Mehling C, Relle L K, Connelly P W, Story J A, Furumoto, E J, Corey P, Wursch P: Effect on blood lipids of very high intakes of fibre in diets low in saturated fat and cholesterol. *N Engl J Med*. 329:21-26,1993

Jenkins D J, Jenkins A L, Wolever, T M, Vuksan V, Rao A V, Thompson L U, Josse R G: Low glycemic index: lente carbohydrates and physiological effects of altered food frequency. *Am J Clin Nutr* 59:706s-709s, 1994

Jenkins D J A, Vuksan V, Wolever T M S, Ransom T P P, Vidgen E, Hegele R A, Leiter L, Josse R G, Abdolell, Patten R, Rao A V, Kendall C W C, Story, J A, Boctor D L, Corey P N: Diet and cardiovascular disease risk reduction: a place for fibre? *Nutr Metab Cardiovasc Dis* 5:251-259, 1995

Johnson C L, Rifkind B M, Sempos C T, Carroll M D, Bachorick P S, Briefel R R, Gordon D J, Burt V L, Brown C D, Lippel K, Cleeman J I: Declining serum total cholesterol levels among US adults: the National Examination Surveys. *JAMA* 269;3002-3008. 1993

Katona G, Aganovic I, Vuksan V, Skrabalo Z: The National Diabetes Programme in Malta: Final Report of Phases I and 11. Geneva, World Health Organization, (NCD/OND/DIAB/83.2) 1983

Kiriyama S, Enishi A, Yoshida A, Suhiyama N, Shimahara H: Hypercholesterolemic activity and molecular weight of *Konjac-mannan*. *Nutr Reports Intl* 6:231-236, 1972

Kiriyama S, Enishi A, Yura K: Inhibitory effect of KJM on bile acid transport in the everted sacs from rat ileum. *J Nutr* 104:69-78, 1974

Kuzuya T, Saito T, Yoshida S: Human C-peptide immunoreactivity (CPR) in blood and urine-Evaluation of radioimmunoassay method and its clinical applications. *Diabetologia* 12:511:518, 1976

Landin K, Holm G, Tengborn L, Smith U: Guar gum improves insulin sensitivity, blood lipids, blood pressure, and fibrinolysis in healthy men. *Am J Clin Nutr* 56:1061-1065, 1992

Liese A D, Mayer-Davis E J, Haffner S M: Development of the insulin resistance syndrome: An Epidemiologic Perspective. Epidemiol Rev 20:157-172, 1998

Livesey J H, Hodgkinson S C, Roud H R, Donald R A: Effect of time, temperature and freezing on the stability of immunoreactive LH, FSH, TSH, growth hormone, prolactin and insulin in plasma. *Clin Biochem* 13:151-157, 1980

Lloyd D, Marples J: Simple Calorimetry of glycated serum protein in a centrifugal analyzer. *Clin Chem* 30:1686-1688, 1984

McNamara J R, Schaefer E J: Automated enzymatic standardization lipid analyses for plasma and lipid fractions. *Clin Chim Acta* 166:108-111, 1987

Matsuda and DeFronzo, Diabetes Care 1999; 22:1462-70

Modan M, Halkin H, Almog S, Lusky A, Eshkol A, Shefi M, Shitrit A, Fuchs Z: Hyperinsulinemia. A link between hypertension, obesity and glucose intolerance. *J Clin Invest* 75:809-817, 1985

Morgan L M, Tredger J A, Wright J, Marks V: The effect of soluble- and insoluble-fibre supplementation on postprandial glucose tolerance, insulin and gastric inhibitory polypeptide secretion in healthy subjects. *Br J Nutr* 64:103-110, 1990

National Cholesterol Education Program: Second report of the expert panel on detection, evaluation, and treatment of high blood cholesterol in adults (adult treatment panel II). *Circulation* 89:1333-1445, 1994

Olson B H, Anderson S M, Becker M P, Anderson J W, Hunninghake D B, Jenkins D J, LaRosa J C, Rippe J M, Roberts D C, Story D B, Summerbell C D, Truswell A S, Wolever T M S, Morris D H, Fulgoni V L 3rd: Psyllium-enriched cereals lower blood total cholesterol and LDL cholesterol, but not HDL cholesterol, in hypercholesterolemic adults: results of a meta-analysis. *J Nutr* 127: 1973-1980, 1997

Prosky L. Asp N G, Furda I, DeVries J W, Schweizer T F, Harland B F: Determination of total dietary fibre in foods and food products: collaborative study. *J Assoc Off Chem* 68:677-679, 1985

Reaven G M (1994) Syndrome X: 6 years later. *J Intern Med* 736:13-22, 1994

Remington's Pharmaceutical Sciences (Remington's Pharmaceutical Sciences, Mack Publishing Company, Easton, Pa., USA 1985)

Rimm E B, Ascherio A, Giovannucci E, Spiegelman D, Stampfer M J, Willeft W C: Vegetable, fruit, and cereal fiber intake and coronary heart disease among men. *JAMA* 275:447-451, 1996

SAS Institute Inc: *SAS/STAT User's guide*. Version 6, 4th ed. Cary NC: SAS Institute Inc, 1989

Salmeron J, Ascherio A, Rimm E B, Colditz G A, Spiegelman D, Jenkins D J, Stampfer M J, Wing A L, Willett W C: Dietary fiber, glycemic load and risk of NIDDM in men. *Diabetes Care* 20:545-550, 1997

Salmeron J, Manson J E, Stampfer M J, Colditz G A, Wing A L, Willeft W C: Dietary fiber, glycemic load and risk of non-insulin-dependent diabetes mellitus in women. *JAMA* 277:472-477, 1997

Schaefer E J, Lichtenstein A H, Lamon-Fava S, Contois J H, Li Z, Rasmussen H, McNamara J R, Ordovas J M: Efficacy of a National Cholesterol Education Program Step 2 Diet in normolipidemic and hypercholesterolemic middle-aged men and elderly men and women. *Arterioscler Thromb Vasc Biol* 15:1079-1083, 1995

Shima K, Tabata M, Tanaka A, Kumahara Y: Effect of dietary fiber (guar gum and *konjac* powder) on diabetic control. *Nutr Report Intl* 26:297-302, 1982

Shima K, Tanaka A, Ikegami H, Tabata M, Sawazaki N, Kumahara Y: Effect of dietary fiber, glucomannan, on absorption of sulfonylurea in man. *Horm Metab Res* 15:1-3, 1983

Salmeron J, Ascherio A, Rimm E B, Colditz G A, Spiegelman D, Jenkins D J, Stampfer M J, Wing A L, Willeft W C: Dietary fiber, glycemic load, and risk of NIDDM in men. Diabetes Care 20:545-50, 1997

Salmeron J, Manson J E, Stampfer M J, Colditz G A, Wing A L, Willeft W C: Dietary fiber, glycemic load and risk of non-insulin-dependent diabetes mellitus in women. *JAMA* 277:4724-77, 1997

Savage P J: Cardiovascular complications of diabetes mellitus: what we know and what we need to know about prevention. *Ann Intern Med* 124:123-126, 1996

Shima K, Tanaka A, Ikegami H, Tabata M, Sawazaki N, Kumahara Y: Effect of dietary fiber, glucomannan, on absorption of sulfonylurea in man. *Horm Metab Res* 15:1-3, 1983

Shima K, Tabata M, Tanaka A, Kumahara Y: Effect of dietary fiber (guar gum and *konjac* powder) on diabetic control. *Nutr Report Intl* 26:297-302, 1982

Stamler J, Vaccaro O, Neaton J D, Wentworth D. Diabetes, other risk factors, and 12 yr cardiovascular mortality for men in the multiple risk factor intervention trial. *Diabetes Care* 16:434-444, 1993

Stefanick M L, Mackey S, Sheehan M, Ellsworth N, Haskell W L, Wood P D: Effects of diet and exercise in men and postmenopausal women with low levels of HDL cholesterol and high levels of LDL cholesterol. *N Engl J Med* 339:12-20, 1998

Swain J F, Rouse I L, Curley C B, Sacks F M: Comparison of the effects of oat bran and low-fibre wheat on serum lipoprotein levels and blood pressure. *N Engl J Med* 322:147-152, 1990

Terasawa F, Tsuji K, Tsuji E, Oshima S, Suzuki S, Seki M: The effects of *konjac* flour on the blood lipids in the elderly subjects. *Japan J Nutr* 37:23-28, 1979

The Agriculture Research Services. *Composition of Foods, Agriculture Handbook* No 8. Washington, DC, US Department of Agriculture, 1992

The Lipid Research Clinics Population Studies Data Book. Vol. 2. The prevalence study-nutrient intake. Washington DC: Government printing office (NIH publication no. 82-2014), 1982

Trevisan M, Liu J, Bahsas F B, Menofti A: Syndrome X and mortality: A Population-based Study. *Am J Epidemiol* 148:958-966, 1998

Tuomilehto J, Silvasti M, Manninen V, Uusitupa M, Aro A: Guar gum and gemfibrozil-an effective combination in the treatment of hypercholesterolemia. *Atherosclerosis* 76:71-77, 1989

UK Prospective Diabetes Study (UKPDS) Group: Effect of intensive blood-glucose control with metformin on complications in overweight patients with type 2 diabetes: UKPDS 34. *Lancet* 352:854-865, 1998

Uuistupa M, Tuomilehto J, Karttunen P, Wolf E: Long term effects of guar gum on metabolic control, serum cholesterol and blood pressure levels in type 2 (non-insulin-dependent) diabetic patients with high blood pressure. *Annals Clin Res*16:126s-131 s, 1984

Venter C S, Kruger H S, Vorster H H, Serfonrein W J, Ubbinik J B, DeVilliers L S: The effects of dietary fibre component *konjac*-glucomannan on serum cholesterol levels of hypercholesterolemic subjects. *Human Nutr: Food Sci and Nutr* 41F:55-61, 1987

Venter C S Vorster H H, Cummings J H: Effects of dietary propionate on carbohydrate and lipid metabolism in healthy volunteers. *Am J Gastroenterol* 85:549-553, 1990

Vuksan V, Jenkins D J A, Spadafora P,. Sievenpiper J L, Owen R, Vidgen E, Brighenti F, Josse R G, Leiter L A, Bruce-Thompson C: *Konjac-mannan* (glucomannan) improves glycemia and other associated risk factors for coronary heart disease in type 2 diabetes: A randomized controlled metabolic trial. *Diabetes Care* 22:913-19,1999

Vuksan V, Sievenpiper J L, Koo V Y Y, et al. American ginseng reduces postprandial glycemia in nondiabetic and diabetic individuals. *Arch Intern Med* 2000;160:1009-13

Vuksan V, Stavro M P, Sievenpiper J L, Beljan-Zdravkovic U, Leiter L A, Josse R G, Zheng Xu. Similar postprandial glycemic reductions with escalation of dose and administration time of American ginseng in type 2 diabetes. *Diabetes Care* 2000;23:1221-6

Vuksan V, Stavro M P, Sievenpiper J L, et al. American ginseng improves glycemia in individuals with normal glucose tolerance: Effect of dose and time escalation. *J Am Coil Nutr*, 2000;19:738-744

Vuksan V, Sievenpiper J L, Xu Z, et al. American ginseng (*Panax quinquefolius L.*) attenuates postprandial glycemia in a time, but not dose, dependent manner in healthy individuals. *Am J Clin Nutr*, in press Vuksan V, Xu Z, Jenkins A L, Beljan-Zdravkovic U, Sievenpiper J L, Leiter L A, Josse R G, Stavro M P. American Ginseng improves long-term glycemic control in Type 2 diabetes: Double-Blind Placebo Controlled Crossover Trial. American Diabetes Association Annual Meeting, *Diabetes* 2000; 49(Suppl 1):A95

Vuksan V, Sievenpiper J L. The variable effects of whole-leaf digitalis is a paradigm of the glycemic effects of ginseng-Reply. *Arch Intern Med,* 2000; 160:3330-1

Warnick G R, Benderson J, Albers J J: Dextran sulfate-$Mg^{+2}$ precipitation procedure for quantitation of high-density lipoprotein cholesterol. *Clin Chem* 28: 1379-1388, 1982

Wei M, Gaskill S P, Heffner S M, Ster M P: Effects of diabetes and level of glycemia on all-cause and cardiovascular mortality: The San Antonio Heart Study. Diabetes Care 21(7):1167-1172, 1998

Wing M, Gaskill S P, Haffner S M, Stern M P: Effects of Diabetes and Level of Glycemia on All-Cause and Cardiovascular Mortality. *Diabetes Care* 21:1167-1172, 1998

Wolever T M, Jenkins D J A, Vuksan V, Jenkins A L, Wong G S, Josse R G: Beneficial effect of low-glycemic index diet in overweight NIDDM subjects. *Diabetes Care* 15(4): 562-564, 1992

World Health Organization Diabetes Mellitus: Report of the World Health Organization Study Group. Technical report No. 727:9-15, 1985

Wood P J: Physicochemical properties and physiological effects of the (1-3)(1-4)-beta-D-glucan from oats. *Adv Exp Med Biol* 270:119-27, 1990

I claim:

1. A method for the treatment of a disorder which benefits from reducing blood glucose in an animal in need thereof comprising administering to the animal a sufficient amount of *konjac-mannan* mixture wherein the *konjac-mannan* mixture is consisting essentially 69-77% *konjac-mannan* and 23-31% of a substance capable of increasing the viscosity of *konjac-mannan* to from about 50% to about 250% of *konjac-mannan* alone, wherein the substance is one or more polysaccharides selected from the group consisting of xanthan, carragenan, acetan, and xyloglucana.

2. A method according to claim 1 wherein the mixture comprises a particle size are larger than about 1000 angstroms.

3. A method according to claim 1 wherein the mixture is administered orally in an amount of about 1 to about 4 grams per day.

4. A method according to claim 3 wherein the mixture is administered either prior to a meal or during the meal.

5. A method according to claim 1 wherein the administration is by a liquid, a powder, or as a part of a food product.

6. The method according to claim 1, wherein the disorder which benefits from reducing blood glucose is diabetes, heart disease, or syndrome X.

7. The method of claim 1, wherein the method increases insulin sensitivity in an animal sensitivity.

8. The method of claim 1 wherein the disorder comprises type 2 diabetes.

9. The method according to claim 1, wherein the method reduces systolic blood pressure or blood cholesterol and lipids, comprising.

10. A method according to claim 1 wherein the *konjac-mannan* mixture comprises *konjac-mannan*, xanthan, and carragenan.

11. A method according to claim 1 wherein the *konjac-mannan* mixture consisting essentially of *konjac-mannan* and xanthan.

12. The method according to claim 1, wherein the animal comprises a human.

13. A method according to claim 1 wherein the *konjac-mannan* mixture consisting essentially of 73-77% *konjac-mannan* and 23-27% xanthan.

* * * * *